US008486994B2

(12) United States Patent
Alberts et al.

(10) Patent No.: US 8,486,994 B2
(45) Date of Patent: Jul. 16, 2013

(54) PRODRUGS OF SUBSTITUTED 1,3-DIOXANES AND THEIR USES

(75) Inventors: Peteris Alberts, Helsingborg (SE); Alexandra Santana Sorensen, Holte (DK)

(73) Assignee: Evolva SA, Allshwil (CH)

( * ) Notice: Subject to any disclaimer, the term of this patent is extended or adjusted under 35 U.S.C. 154(b) by 568 days.

(21) Appl. No.: 12/523,849

(22) PCT Filed: Jan. 18, 2008

(86) PCT No.: PCT/US2008/051525
§ 371 (c)(1),
(2), (4) Date: Dec. 8, 2009

(87) PCT Pub. No.: WO2008/089464
PCT Pub. Date: Jul. 24, 2008

(65) Prior Publication Data
US 2010/0087517 A1    Apr. 8, 2010

Related U.S. Application Data

(63) Continuation-in-part of application No. PCT/US2007/002542, filed on Jan. 18, 2007.

(60) Provisional application No. 60/989,805, filed on Nov. 21, 2007, provisional application No. 60/989,808, filed on Nov. 21, 2007, provisional application No. 60/989,806, filed on Nov. 21, 2007.

(51) Int. Cl.
*A61K 31/335* (2006.01)
*C07D 319/06* (2006.01)

(52) U.S. Cl.
USPC ............................ 514/452; 549/373; 549/375

(58) Field of Classification Search
USPC ................................ 549/373, 375; 514/452
See application file for complete search history.

(56) References Cited

U.S. PATENT DOCUMENTS

| | | | |
|---|---|---|---|
| 4,567,197 A | 1/1986 | Brewster et al. |
| 4,723,037 A | 2/1988 | Harris |
| 4,745,198 A | 5/1988 | Brewster et al. |
| 4,775,685 A | 10/1988 | Brewster et al. |
| 4,895,962 A | 1/1990 | Brewster et al. |
| 4,908,380 A | 3/1990 | Brewster et al. |
| 5,128,359 A | 7/1992 | Bru-Magniez et al. |
| 5,166,377 A | 11/1992 | Brewster et al. |
| 5,248,780 A | 9/1993 | Brewster et al. |
| 5,312,818 A | 5/1994 | Rubin et al. |
| 5,462,726 A | 10/1995 | Lodge |
| 5,801,195 A | 9/1998 | Muller et al. |
| 5,981,586 A | 11/1999 | Pershadsingh |
| 6,277,884 B1 | 8/2001 | de Tejada |
| 6,284,790 B1 | 9/2001 | Gupte |
| 6,291,496 B1 | 9/2001 | Dannenberg et al. |
| 6,436,997 B1 | 8/2002 | de Tejada |
| 6,509,348 B1 | 1/2003 | Ogletree |
| 6,951,882 B2 | 10/2005 | Carruthers et al. |
| 2003/0109543 A1 | 6/2003 | Ogletree |
| 2010/0168169 A1 | 7/2010 | Sorensen et al. |

FOREIGN PATENT DOCUMENTS

| | | |
|---|---|---|
| DE | 4225488 | 2/1994 |
| EP | 0094239 | 11/1982 |
| EP | 0201352 | 11/1986 |
| EP | 0337739 | 10/1989 |
| EP | 0365328 | 4/1990 |
| EP | 1028113 | 8/2000 |
| EP | 1267171 | 12/2002 |
| EP | 0266980 | 8/2010 |
| WO | 95/01177 | 1/1995 |
| WO | 96/41013 | 12/1996 |
| WO | 97/10813 | 3/1997 |
| WO | 97/25042 | 7/1997 |
| WO | 97/28149 | 8/1997 |
| WO | 98/43081 | 10/1998 |
| WO | 99/50664 | 10/1999 |
| WO | 99/62509 | 12/1999 |
| WO | 00/30683 | 6/2000 |
| WO | 01/32167 | 5/2001 |
| WO | 01/89519 | 11/2001 |
| WO | 01/95895 | 12/2001 |
| WO | 2004/060282 | 7/2004 |
| WO | 2005/040128 | 5/2005 |
| WO | WO 2005/077943 A1 | 8/2005 |
| WO | 2007/021460 A2 | 2/2007 |
| WO | 2007/138485 | 12/2007 |
| WO | 2008/089461 | 7/2008 |
| WO | 2008/089462 | 7/2008 |
| WO | 2008/089463 | 7/2008 |
| WO | 2008/089464 | 7/2008 |
| WO | 2009/089098 | 7/2009 |

OTHER PUBLICATIONS

PCT International Search Report and Written Opinion, PCT/US2008/051525, Jun. 27, 2008, 7 pages.

Fitzpatrick, Francis A., et al., "Influence of Thromboxane Synthetase Inhibitors on Virus Replication in Human Lung Fibroblasts in Vitro," Biochemical and Biophysical Research Communications, Oct. 1983, vol. 116, No. 1, pp. 264-271.

Foster, M.R., et al., "Effect of GR32191 and Other Thromboxane Receptor Blocking Drugs on Human Platelet Deposition onto De-Endothelialized Arteries," Thrombosis Research, 1992, vol. 65, No. 6, pp. 769-784.

(Continued)

*Primary Examiner* — Andrew D Kosar
*Assistant Examiner* — Raymond Covington
(74) *Attorney, Agent, or Firm* — McDonnell Boehnen Hulbert & Berghoff LLP

(57) ABSTRACT

The present invention relates to prodrugs of compounds containing 1,3-dioxane moiety, pharmaceutical compositions thereof, and the use of the compounds and compositions for the modulation of thromboxane A2 or a peroxisome proliferator-activated receptor. The prodrugs of the compounds, analogs, and pharmaceutically acceptable salts thereof, and pharmaceutical compositions can be used in the treatment and prevention of cancer.

18 Claims, No Drawings

OTHER PUBLICATIONS

Ackerley et al., "A Novel Approach to Dual-Acting Thromboxane Receptor Antagonist/Synthase Inhibitors Based on the Link of 1,3-Dioxane-Thromboxane Receptor Antagonists and -Thromboxane Synthase Inhibitors," J. Med. Chem., 38:1608-1628 (1995).

Adams et al., "Activators of Peroxisome Proliferator-activated Receptor γ Have Depot-specific Effects on Human Preadipocyte Differentiation," J. Clin. Invest, 100(12):3149-3153 (Dec. 1997).

Al-Salman et al., "Hepatocellular Injury in a Patient Receiving Rosiglitazone," Ann. Intern Med., 132:121-124 (Jan. 18, 2000).

Anzick et la., "AIB1, a Steroid Receptor Coactivator Amplified in Breast and Ovarian Cancer," Science, 277:965-968 (1997).

Beauregard et al., "Peroxisome Proliferator-Activated Receptor Agonists Inhibit Interleukin-1β-Mediated Nitric Oxide Production in Cultured Lacrimal Gland Acinar Cells," J. Ocular Pharm. and Therapeutics, 19:579-587 (Nov. 6, 2003).

Berge et al., "Pharmaceutical Salts," Journal of Pharmaceutical Sciences, 66(1):1-19 (Jan. 1977).

Bonazzi et al., "Regulation of Cyclooxygenase-2 by Hypoxia and Peroxisome Proliferators in the Corneal Epithelium," J. Biol. Chem., 275(4):2837-2844 (Jan. 28, 2000).

Börsch-Haubold et al., "Direct Inhibition of Cycloxygenase-1 and -2 by the Kinase Inhibitors SB 203580 and PD 98059," J. Biol. Chem., 273(44):28766-28772 (Oct. 30, 1998).

Boukamp et al., "Normal Keratinization in a Spontaneously Immortalized Aneuploid Human Keratinocyte Cell Line," J. Cell Biol., 273(44):28766-28772 (1988).

Brown et al., "Improved synthetic routes to the novel thromboxaine receptor antagonist ICI 192605: activity of synthetic 1,3-dioxane intermediates," J. Pharm. Pharmacol., 42:53-55 (1990).

Brown et al., "X-Ray Crystal Structure of a Ligand at the Thromboxane A2/Prostaglandin H2 Receptor Site: (4Z)-6-[(2RS,4RS,5SR)-2-92-Chlorophenyl)-4-(2-hydroxyphenyl)-1,3-dioxan-5-yl]hex-4-enoic Acid," J. Chem. Soc. Perkin Trans., 2158-2160 (1990).

Brown et al., "Design of Dual-Acting Thromboxane Antagonist-Synthase Inhibitors by a Mutual Prodrug Approach," Bioorganic & Medicinal Chemistry Letters, 6(3):273-278 (1996).

Brown et al., "ICI 180080, a novel selective thromboxane receptor antagonist: synthesis and relative activity," J. Pharm. Pharmacol., 38:706-708 (1986).

Bueno et al., "L-carnitine and propionyl-L-carnitine improve endothelial dysfunction in spontaneously hypertensive rats: Different participation of NO and COX-products," Life Sciences, 77:2082-2097 (2005).

Carroll et al., "A thrombelastograph whole blood assay for clinical monitoring of NSAID-insensitive transcellular platelet activation by arachidonic acid," J. Lab. Clin. Med. 146(1):30-35 (Jul. 2005).

Castillo et al., "An adipogenic cofactor bound by the differentiation domain of PPARγ," The EMBO Journal, 18 (13):3676-3687 (1999).

Casy et al., "HPLC and 1H-NMR study of chiral recognition in some thromboxane antagonists induced by β-cyclodextrin," J. Pharm. & Biomed. Analysis, 9(10-12):787-792 (1991).

Chakravarti et al., "Role of CBP/P300 in nuclear receptor signalling," Nature, 383:99-103 (Sep. 5, 1996).

Chen et al., "A transcriptional co-repressor that interacts with nuclear hormone receptors," Nature, 377:454-457 (Oct. 5, 1995).

Cheng-Lai et al., "Rosiglitazone—An Agent from the Thiazolidinedione Class for the Treatment of Type 2 Diabetes," Heart Disease, 2:326-333 (2000).

Crankshaw, Denis, "Effects of the isoprostante, 8-3pi-prostaglandin F2α, on the contractility of the human myometrium in vitro," European Journal of Pharmacology, 285:151-158 (1995).

Daray et al., "Pharmacological characterization of prostanoid receptors mediating vasoconstriction in human umbilical vein," British Journal of Pharmacology, 139:1409-1416 (2003).

de Graaf et al., "Molecular modeling of the second extracellular loop of G-protein coupled receptors and its implication on structure-based virtual screening," Proteins, 71:599-620 (2008).

Kristiansen et al., U.S. Appl. No. 12/161,317, filed Jul. 17, 2008.

Dowell et al., "Identification of Nuclear Receptor Corepressor as a Peroxisome Proliferator-activated Receptor α Interacting Protein," J. Biol. Chem., 274(22):15901-15907 (May 28, 1999).

Dowell et al., "p300 Functions as a Coactivator for the Peroxisome Proliferator-activated Receptor α," J. Biol. Chem., 272(52):33435-33443, (Dec. 26, 1997).

Duez et al., "PPARs in inflammation, atherosclerosis and thrombosis," Journal of Cardiovascular Risk, 8(4):185-186 (Aug. 2001).

Elbrecht et al., "Molecular Cloning, Expression and Characterization of Human Peroxisome Proliferator Activated Receptors γ1 and γ2," Biochemical and Biophysical Research Communications, 224:431-437 (1996).

Ettmayer et al., "Lessons Learned from Marketed and Investigational Prodrugs," J. Med. Chem., 47(10):2393-2404 (May 6, 2004).

Faull et al., "Dual-Acting Thromboxane Receptor Antagonist/ Synthase Inhibitors: Synthesis and Biological Properties of [2-Subsituted-4-(3-pyridyl)-1,3-dioxan-5-yl]alkenoic Acids," J. Med. Chem., 38:686-694 (1995).

International Search Report for WO 2008/089463 mailed on Jun. 27, 2008.

International Search Report for WO 2008/089462 mailed on Jul. 2, 2008.

Brewster et al., "(5Z)-7-(2,2-Dimethyl-4-phenyl-1,3-dioxan-cis-5-yl)heptenoic Acid: A Specific Thromboxane A2 Receptor Antagonist," J. Med. Chem., 30:67-70 (1987).

Brewster et al., "The Synthesis of a Novel Thromboxane Receptor Antagonist 4(Z)-6-(2-O-Cholorophenyl-4-O-Hydroxyphenyl-1,3,Dioxan-CIS-5-YL) Hexenoic Acid ICI 192605," Prostaglandins, 36(2):173-178 (Aug. 1988).

CID9978509, PubChem Public Chemical Database, 2 pages, Oct. 25, 2006.

Sorensen et al., U.S. Appl. No. 12/523,848, filed Jul. 7, 2010.

Sorensen et al., U.S. Appl. No. 12/523,844, filed Jul. 20, 2009.

Forman et al., "Hepatic Failure in a Patient Taking Rosiglitazone," Ann. Intern Med. 132:118-121 (Jan. 18, 2000).

Gale et al., "Lessons from the glitazones: a story of drug development," Lancet, 357:1870-1875 (Jun. 9, 2001).

Gao et al., "Hydrogen peroxide induces a greater contraction in mesenteric arteries of spontaneously hypertensive rats through thromboxane A2 production," British Journal of Pharmacology, 134:1639-1646 (2001).

Glass et al., "The coregulator exchange in transcriptional functions of nuclear receptors," Genes & Development, 14:121-141 (2000).

Hall, Steven E., "Thromboxane A2 Receptor Antagonists," Medicinal Research Reviews, 11(5):503-579 (1991).

Haskins et al., "Thiazolidinedione toxicity to isolated hepatocytes revealed by coherent multiprobe fluorescence microscopy and correlated with multiparameter flow cytometry of peripheral leukocytes," Arch Toxicol., 75:425-438 (2001).

Hedberg et al., Characterization of [5,6-3H]SQ 29,548 as a High Affinity Radioligand, Binding to Thromboxane A2/Prostaglandin H2-Receptors in Human Platelets, J. Pharm. & Exp. Ther., 245(3):786-792 (1988).

Heinlein et al., "Identification of ARA70 as a Ligand-enhanced Coactivator for the Peroxisome Proliferator-activated Receptor γ," J. Biol. Chem., 274(23):16147-16152 (Jun. 4, 1999).

Helledie et al., "Lipid-binding proteins modulate ligand-dependent transactivation by peroxisome proliferator-activated receptors and localize to the nucleus as well as the cytoplasm," Journal of Lipid Research, 41:1740-1751 (2000).

Hutchinson et al., "Effects of eicosanoids on parameters in isolated rat hepatocytes and isolated rate hepatocyte couplets: protective effects of eiocsanoid receptor antagonists," J. Lipid Mediators Cell Signalling, 15:249-254 (1997).

Iizuka et al., "Highly Selective Inhibitors of Thromboxane Synthetase. 1. Imidazole Derivatives," J. Med. Chem., 24:1139-1148 (1981).

Janssen et al., "Vasoconstrictor actions of isoprostanes via tyrosine kinase and Rho kinase in human and canine pulmonary vascular smooth muscles," British Journal of Pharmacology, 132:127-134 (2001).

Jourdan et al., "Evidence for a dilator function of 8-iso prostaglandin F2α in rat pulmonary artery," British Journal of Pharmacology, 120:1280-1285 (1997).

Kaplan et al., "PPARs, insulin resistance and type 2 diabetes," J. Cardiovascular Risk, 8:211-217 (2001).

Kawikova et al., "Bradykinin-induced release of thromboxane B2 into bronchoalveolar lavage fluid of guinea pigs: relationship to airflow obstruction," Eur. Journal of Pharmacology, 280:293-299 (1995).

Kawikova et al., "U46619 (a Thromboxane A2 Mimetic) Induces Airflow Obstruction and Airway Plasma Extravasation in the Guinea Pig: The Role of Histamine, Cyclooxygenase Metabolites, Leukotrienes and PAF," J. Pharm. & Exp. Therapeutics, 278(1):268-276 (1996).

Kodera et al., "Ligand type-specific Interactions of Peroxisome Proliferator-activated Receptor γ with Transcriptional Coactivators," J. Biol. Chem., 275(43):33201-33204 (2000).

Kopelovich et al., "Peroxisome Proliferator-activated Receptor Modulators As Potential Chemopreventive Agents," Molecular Cancer Therapeutics, 1:357-363 (Mar. 2002).

Landreth et al., "Anti-inflammatory actions of peroxisome proliferator-activated receptor gamma agonists in Alzheimer's disease," Neurobiology of Aging, 22:937-944 (2001).

Lanz et al., "A Steroid Receptor Coactivator, SRA, Functions as an RNA and is Present in an SRC-1 Complex," Cell, 97:17-27 (Apr. 2, 1999).

Lavinsky et al., "Diverse signaling pathways modulate nuclear receptor recruitment of N-CoR and SMRT complexes," PNAS USA, 95:2920-2925 (Mar. 1998).

Lebovitz, Harold E., "Differentiating members of the thiazolidinedione class: a focus on safety," Diabetes/Metabolism Research and Reviews, 18:S23-S29 (2002).

Lehmann et al., "An Antidiabetic Thiazolidinedione Is a High Affinity Ligand for Peroxisome Proliferator-activated Receptor γ (PPARγ)," J. Biol. Chem., 270(22):12953-12956 (Jun. 2, 1995).

Nagai et al., "Factor V Leiden mutation is associated with enhanced arterial thrombotic tendency in lean but not in obese mice," Thromb Haemost, 98:858-863 (2007).

Onate et al., "Sequence and Characterization of a Coactivator for the Steroid Hormone Receptor Superfamily," Science, 270:1354-1357 (Nov. 24, 1995).

Patscheke et al., "Investigations on a Selective Non-Prostanoic Thromboxane Antagonist, BM 13.177, in Human Platelets," Thrombosis Research, 33:277-288 (1984).

Pineda Torra, Ines et al., "Peroxisome proliferator-activated receptor alpha in metabolic disease, inflammation, atherosclerosis and aging," Current Opin. in Lipidology, 10:151-159 (1999).

Puigserver et al., "A Cold-Inducible Coactivator of Nuclear Receptors Linked to Adaptive Thermogenesis," Cell, 92:829-839 (Mar. 20, 1993).

Rachez et al., "Ligand-dependent transcription activation by nuclear receptors requires the DRIP complex," Nature, 398:824-828 (Apr. 29, 1999).

Rhee et al., "Active Conformation of Thromboxane A2 and Thromboxane A2 Receptor Antagonists," J. Pharm. Soc. 41(6):765-772 (1997) English Abstract Only.

Rumi et al., "Can PPARγ Ligands Be Used in Cancer Therapy?" Curr. Med. Chem—Anti-Cancer Agents, 4:465-477 (2004).

Saussy Jr. et al., "Identification of a Putative Thromboxane A2/PRostaglandin H2 Receptor in Human Platelet Membranes," J. Biol. Chem., 261(7):3025-3029 (1996).

Scheen, A. J., "Thiazolidinediones and Liver Toxicity," Diabetes Metab (Paris), 27:305-313 (2001).

Senchyna et al., "Characterizatin of the Prostanoid TP Receptor Population in Human Nonpregnant Myometrium," J. Pharm. and Exp. Therapeutics, 279(1):262-270 (1996).

Shaw et al., "Combined administration of 5-HT2 and thromboxane A2 antagonists: effects on platelet aggregation and isolated cardiac muscle," British Journal of Pharmacology, 121:875-882 (1997).

Shaw et al., "Erratum," British Journal of Pharmacology, 120:1186 (1997).

Shaw et al., "Erratum," British Journal of Pharmacology, 118:1326 (1996).

Shaw et al., "Suppression of reperfusion-induced arrhythmias with combined administration of 5-HT2 and thromboxane A2 antagonists," British Journal of Pharmacology, 117:817-822 (1996).

Smith et al., "Peroxisomes in Dermatology. Part I," J. Cutan. Med. Surg., 231-243 (2001).

Soon Tan et al., "Peroxisome proliferator-activated receptor-β as a target for wound healing drugs," Expert Opin. Ther. Targets 8(1):39-48 (2004).

Treuter et al., "A Regulatory Role for RIP140 in Nuclear Receptor Activation," Mol. Endocrinol., 12:864-881 (1998).

Wermuth et al., "Molecular Variations Based on Isosteric Replacements," The Practice of Medicinal Chemistry, Academic Press, pp. 233-237 (1996).

Xie, G. et al., "5-Hydroxytryptyamine-induced plasma extravasation in the rat knee joint is mediated by multiple prostaglandins," Inflammation Research, 52:32-38 (2003).

Yamamoto, Y. et al., "Cytotoxicity and apoptosis produced by troglitazone in human hepatoma cells," Life Sciences, 70:471-482 (2001).

Zhu et al., "Isolation and Characterization of PBP, a Protein That Interacts with Peroxisome Proliferator-activated Receptor," 272(41):25500-25506 (Oct. 10, 1997).

Zhu et al., "Isolation and Characterization of Peroxisome Proliferator-activated Receptor (PPAR) Interacting Protein (PRIP) as a Coactivator for PPAR," J. Biol. Chem., 275(18):13510-13516 (2000).

Allen, Graham D., "Modfit: a pharmacokinetics computer program," Biopharmaceutics & Drug Disposition, 11:477-498 (1990).

International Search Report for WO 2007/138485 mailed on Feb. 12, 2008.

International Search Report for WO 2008/089461 mailed on May 21, 2008.

Ding et al., "Lipoxygenase and cyclooxygenase metabolism: new insights in treatment and chemoprevention of pancreatic cancer," Molecular Cancer, 2:1-12 (Jan. 7, 2003) http://www.molecular-cancer.com/content/2/1/10.

PRODRUGS OF SUBSTITUTED 1,3-DIOXANES AND THEIR USES

This application is the National Stage of and claims priority to International Application No. PCT/US2008/051525, filed Jan. 18, 2008, and claims benefit of PCT Application No. PCT/IB/2007/002542, filed Jan. 18, 2007, U.S. provisional Application No. 60/989,808, filed on Nov. 21, 2007, U.S. provisional Application No. 60/989,806, filed on Nov. 21, 2007, and U.S. provisional Application No. 60/989,805, filed on Nov. 21, 2007, all of which are incorporated by reference in their entirety.

CROSS-REFERENCE TO RELATED APPLICATIONS

This application claims the benefit of and claims priority from U.S. provisional Application Ser. No. 60/989,805, filed Nov. 21, 2007, U.S. provisional Application Ser. No. 60/989,806, filed Nov. 21, 2007, U.S. provisional Application Ser. No. 60/989,808, filed Nov. 21, 2007, and PCT Application No. PCT/US07/60724, filed Jan. 18, 2007, all of which are incorporated herein by reference in their entirety.

FIELD OF INVENTION

The invention relates to prodrugs containing the 1,3-dioxane moiety, compositions comprising the compounds, and methods of using the compounds and compositions for the modulation of thromboxane A2 and/or peroxisome proliferator-activated receptors. The compounds and compositions are useful for treating or modulating disease in which thromboxane A2 and/or peroxisome proliferator-activated receptors may be involved, symptoms of such disease, or the effect of other physiological events mediated by thromboxane A2 and/or peroxisome proliferator-activated receptors.

BACKGROUND OF THE INVENTION

Peroxisome proliferator-activated receptors (PPAR) are nuclear hormone receptors. PPAR receptors activate transcription by binding to elements of DNA sequences, known as peroxisome proliferator response elements (PPRE), in the form of a heterodimer with retinoid X receptors (known as RXRs). Three sub-types of human PPAR have been identified and described: PPAR-alpha, PPAR-gamma and PPAR-delta (or NUCI). PPAR-alpha is mainly expressed in the liver, while PPAR-delta is ubiquitous. PPAR-gamma is involved in regulating the differentiation of adipocytes, where it is highly expressed. It also has a key role in systemic lipid homeostasis. A number of compounds that modulate the activity of PPARs have been identified including thiazolidinediones, which have been employed in the treatment of diabetes.

The DNA sequences of the PPAR-gamma subtypes are described in Elbrecht et al., BBRC 224; 431-437 (1996). Peroxisome proliferators including fibrates and fatty acids activate the transcriptional activity of PPARs.

Numerous examples are provided in the literature illustrating that PPARs are closely involved in a wide array of diseases or pathological conditions which are associated with cells expressing these nuclear receptors. More specifically, PPARs are useful as drug target in methods for reducing blood glucose, cholesterol and triglyceride levels and are accordingly explored for the treatment and/or prophylaxis of insulin resistance, dyslipidemia, and other disorders related to Syndrome X (also designated "the metabolic syndrome) (WO 97/25042, WO 97/10813, WO 97/28149; see also Kaplan et al., 2001, J Cardiovasc Risk, 8, 211-7) including obesity and atherosclerosis (Duez et al., 2001, J. Cardiovasc. Risk, 8, 185-186), coronary artery disease and certain other cardiovascular disorders. Further, PPARs have been shown to be potential targets for the treatment of certain inflammatory diseases such as cutaneous disorders (see Smith et al., 2001, J. Cutan. Med. Surg., 5, 231-43), gastrointestinal diseases (WO 98/43081) or renal diseases including glomerulonephritis, glomerulosclerosis, nephrotic syndrome and hypertensive nephrosclerosis. Similarly PPARs are useful for improving cognitive functions in neurologic diseases (Landreth and Heneka, 2001, Neurobiol Aging, 22, 937-44) or in dementia, for treating psoriasis, polycystic ovarian syndrome (PCOS) or for preventing and treating bone loss, e.g. osteoporosis (see for example U.S. Pat. No. 5,981,586 or U.S. Pat. No. 6,291, 496).

Thus, PPARs are exciting targets for the development of therapeutic compounds. Although, the responses observed in the context of the various methods for treating and/or preventing diseases or pathological conditions are encouraging, for example, the thiazolidinedione, TZD, class of medications (e.g., rosiglitazone or pioglitazone) unambiguously plays a critical role in improving insulin sensitivity in patients with type 2 diabetes (see Cheng lai and Levine, 2000, Heart Dis., 2, 326-333), they are not fully satisfactory treatments because of the occurrence of numerous serious undesirable side effects (for example, weigh gain, hypertension, cardiac hypertrophy, haemodilution, liver toxicity and oedema; see Haskins et al., 2001, Arch Toxicol., 75, 425-438; Yamamoto et al., 2001, Life Sci., 70, 471-482; Scheen, 2001, Diabetes Metab., 27, 305-313; Gale, 2001, Lancet, 357, 1870-1875; Forman et al., 2000, Ann. Intern. Med., 132, 118-121 and Al Salman et al., 2000, Ann. Intern. Med., 132, 121-124). Consequently, it is desirable to identify novel improved products and/or novel methods which enable the treatment and/or the prevention of diseases or pathological conditions associated with cell types that express PPAR nuclear receptors. More specifically, most of the side effects observed with TZD derivatives are attributable to the full-agonist properties of said compounds and thus it is desirable to identify new compounds that are not necessarily full-agonists.

The thromboxane receptor is involved in blood platelet aggregation and has been implicated in vasoconstriction, as well as in bronchial and tracheal smooth muscle constriction. European patent application, publication No. 94239; European patent application, Publication No. 0 266 980 and U.S. Pat. No. 4,895,962 name certain 4-phenyl-1,3-dioxan-5-ylalkenoic acid derivatives and describe their potential utility as thromboxane receptor antagonists.

The development of selective modulators of thromboxane A2 and/or peroxisome proliferator-activated receptors that can block the disease pathologies and/or symptoms resulting from their aberrant activity has generated much interest. However, additional compounds as modulators of thromboxane A2 and/or peroxisome proliferator-activated receptors (PPAR) and treatment and prevention of diseases associated with them are needed.

SUMMARY OF THE INVENTION

The present invention provides prodrugs of compounds having the 1,3-dioxane moeity, compositions comprising the compounds, methods and intermediates useful for synthesizing the compounds and methods of using the compounds, including in the treatment and/or prevention of diseases mediated by thromboxane A2 and/or peroxisome proliferator-activated receptors (PPAR).

The compounds of the invention are potent modulators of thromboxane A2 and/or peroxisome proliferator-activated receptor. Accordingly, in still another aspect, the present invention provides methods of using the compounds as any of the PPAR agonists, TP receptor antagonists, thromboxane synthase (TS) inhibitors comprising contacting a receptor with an effective amount of a compound or composition of the invention effective for modulation. The methods can be practiced either in vitro or in vivo, and can be used as a therapeutic approach towards the treatment and/or prevention of diseases such as treatment of neoplasia including cancer and metastasis, and in the treatment and prevention of other diseases associated with thromboxane A2 or peroxisome proliferator-activated receptors.

Compounds of the present invention are useful for, but not limited to, the prevention or treatment of cancer and related diseases. The compounds of the invention have thromboxane A2 inhibitory and/or peroxisome proliferator-activated receptors activation activity, therefore, the compounds of the invention can be useful in therapy as antineoplasia agents. Compounds of the invention can be useful for the treatment of obesity, diabetes and the commonly associated disorders such as cardiovascular and hepatic disease.

The compounds of this invention can act as inhibitors of thromboxane A2 and/or activate peroxisome proliferator-activated receptors (PPAR), and thus be effective in the treatment of diseases associated with these receptors. These compounds may for example be useful in the treatment or prevention of a clinical condition selected from the group consisting of the metabolic syndrome, obesity, insulin resistance, pre-diabetes, diabetes, dyslipidemia, autoimmune disease such as multiple sclerosis, psoriasis, atopic dermatitis, asthma and ulcerative colitis, cancer such as liposarcoma, neuroblastoma, bladder, breast, colon, lung, pancreas and prostate; inflammation, infections, AIDS and wound healing.

In addition these compound may for example be useful in the treatment or prevention of a clinical condition is selected from the group consisting of myocardial infarction, thrombosis, thrombotic disorders, pulmonary hypertension, atherosclerosis, diabetic nephropathy, retinopathy, peripheral arterial disease, lower limb circulation, pulmonary embolism, thrombus formation, stent-triggered thrombus formation, stent induced restenosis, hyperplasia, stent-triggered hyperplasia, septic shock, preeclampsia, asthma, rhinitis, allergic rhinitis, tumour angiogenesis and metastasis.

In one aspect, the present invention provides prodrugs of compounds containing the 1,3-dioxane moiety, particularly diaryl 1,3-dioxane moiety, and compositions comprising the compounds. The compounds containing the 1,3-dioxane moiety have the general structure shown below:

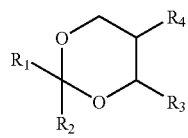

(I)

where $R_1$, $R_2$, $R_3$, and $R_4$ can be independently selected to be hydrogen, halo, halo alkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl or heteroaryl.

In one aspect of the invention, the invention provides prodrugs of formula (III)

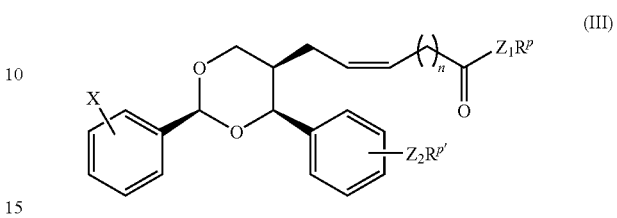

(III)

where X can be hydrogen, halogen, cyano, nitro, hydroxyl, haloalkyl, alkyl, or O—R where R is a lower alkyl group; n can be 0, 1, 2, 3, 4, or 5; $Z_1$ and $Z_2$ can be independently selected to be O, N, or S, and $R^p$ and $R^{p'}$ can be independently selected from H, lower alkyl, or a progroup. The prodrugs can thus be compounds where both $Z_1$ and $Z_2$ can be O, and at least one of $R^p$ or $R^{p'}$ is a progroup such as lower alkyl, ester, amide, and the like. The progroup $R^p$ or $R^{p'}$ can be metabolized in vivo to yield the active diaryl 1,3-dioxane moiety containing drug The prodrugs and compositions can be used in methods for the inhibition of thromboxane A2 and/or activation of PPAR.

In another aspect, the present invention provides methods of treating and/or preventing cancer. The methods generally involve administering to a subject that has cancer or that is at risk of developing cancer an amount of a compound or composition of the invention effective to treat or prevent the disease. The method may be practiced in animals or in humans.

DETAILED DESCRIPTION OF THE PREFERRED EMBODIMENTS

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art.

As used herein, the following terms are intended to have the following meanings:

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl; pentanyls, such as pent-1-yl, pent-2-yl, pent-3-yl, cyclopent-1-yl; hexanyls, such as hexan-1-yl, hexan-3-yl, cyclohexan-1-yl, etc.; heptanyls, such as heptan-1-yl, heptan-2-yl, cycloheptan-1-yl, etc,; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms (C1-C6 alkyldiyl). Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkoxy," by itself or as part of another substituent, refers to a radical of the formula —OR, where R is an alkyl or cycloalkyl group as defined herein. Representative examples alkoxy groups include, but are not limited to, methoxy, ethoxy, propoxy, isopropoxy, butoxy, tert-butoxy, cyclopropyloxy, cyclopentyloxy, cyclohexyloxy and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms ($C_6$-$C_{20}$ aryl), more preferably from 6 to 15 carbon atoms ($C_6$-$C_{15}$ aryl) and even more preferably from 6 to 10 carbon atoms ($C_6$-$C_{10}$ aryl).

"Aryloxy," by itself or as part of another substituent, refers to a radical of the formula —O-aryl, where aryl is as defined herein.

"Aryloxycarbonyl," by itself or as part of another substituent, refers to a radical of the formula —C(O)—O-aryl, where aryl is as defined herein.

"Compounds of the invention" refers to compounds encompassed by the various descriptions and structural formulae disclosed herein. The compounds of the invention may be identified by either their chemical structure and/or chemical name. When the chemical structure and chemical name conflict, the chemical structure is determinative of the identity of the compound. The compounds of the invention may contain one or more chiral centers and/or double bonds and therefore may exist as stereoisomers, such as double-bond isomers (i.e., geometric isomers), rotamers, enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures, with the exception that when only one enantiomer is specified, the structure includes the other enantiomer as well. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention may also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl. Compounds of the invention may exist in unsolvated forms as well as solvated forms, including hydrated forms and as N-oxides. In general, the hydrated, solvated and N-oxide forms are within the scope of the present invention. Certain compounds of the present invention may exist in multiple crystalline or amorphous forms. In general, all physical forms are equivalent for the uses contemplated by the present invention and are intended to be within the scope of the present invention.

"Cycloalkyl," by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, cycloheptane, and the like. Preferably, the cycloalkyl group comprises from 3 to 10 ring atoms ($C_3$-$C_{10}$ cycloalkyl) and more preferably from 3 to 7 ring atoms ($C_3$-$C_7$ cycloalkyl).

"Cycloheteroalkyl," by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. Preferably, the cycloheteroalkyl group comprises from 3 to 10 ring atoms (3-10 membered cycloheteroalkyl) and more preferably from 5 to 7 ring atoms (5-7 membered cycloheteroalkyl).

"Halogen" or "Halo," by themselves or as part of another substituent, refer to a fluoro, chloro, bromo and/or iodo radical.

"Haloalkyl," by itself or as part of another substituent, refers to an alkyl group as defined herein in which one or more of the hydrogen atoms is replaced with a halo group. The term "haloalkyl" is specifically meant to include monohaloalkyls, dihaloalkyls, trihaloalkyls, etc. up to perhaloalkyls. The halo groups substituting a haloalkyl can be the same, or they can be different. For example, the expression "($C_1$-$C_2$) haloalkyl" includes 1-fluoromethyl, 1-fluoro-2-chloroethyl, difluoromethyl, trifluoromethyl, 1-fluoroethyl, 1,1-difluoroethyl, 1,2-difluoroethyl, 1,1,1-trifluoroethyl, perfluoroethyl, etc.

"Haloalkyloxy," by itself or as part of another substituent, refers to a group of the formula —O-haloalkyl, where haloalkyl is as defined herein.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group comprises from 5 to 20 ring atoms (5-20 membered heteroaryl), more preferably from 5 to 10 ring atoms (5-10 membered heteroaryl). Preferred heteroaryl groups are those derived from furan, thiophene, pyrrole, benzothiophene, benzofuran, benzimidazole, indole, pyridine, pyrazole, quinoline, imidazole, oxazole, isoxazole and pyrazine.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

"Pharmaceutically acceptable vehicle" refers to a diluent, adjuvant, excipient or carrier with which a compound of the invention is administered.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active compound (drug) that undergoes a transformation under the conditions of use, such as within the body, to release an active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety or "progroup" which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature, or combination thereof. The agent may be endogenous to the conditions of use, such as an enzyme present in the cells to which the prodrug is administered or the acidic conditions of the stomach, or it may be supplied exogenously.

A wide variety of progroups suitable for masking functional groups in active compounds to yield prodrugs are well-known in the art. For example, a hydroxyl functional group may be masked as a sulfonate, ester or carbonate promoiety, which may be hydrolyzed in vitro to provide the hydroxyl group. An amino functional group may be masked as an amide, imine, phosphinyl, phosphonyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active drug, converts the drug into a prodrug. Progroups are typically attached to the functional group of the drug via bonds that are cleavable under specified conditions of use.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2O^-$, —$(CH_2)_{0-4}S(O)_2OR^b$, —$OS(O)_2R^b$, —$OS(O)_2O^-$, —$OS(O)_2 OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

As used herein, the terms "treat" or "treatment" are used interchangeably and are meant to indicate a postponement of development of a disease and/or a reduction in the severity of such symptoms that will or are expected to develop, where the disease is associated with the functioning of a kinase. The terms further include ameliorating existing symptoms, preventing additional symptoms, and ameliorating or preventing the underlying metabolic causes of symptoms.

The compounds of the present invention may be used to modulate the activity of thromboxane A2 and/or PPAR. The compounds can be PPAR agonists, TP receptor antagonists, or TS inhibitors. In these contexts, inhibition and reduction of activity of the receptors refers to a lower level of the measured activity relative to a control experiment in which the cells or the subjects are not treated with the test compound. In particular aspects, the inhibition or reduction in the measured activity is at least a 10% reduction or inhibition. One of skill in the art will appreciate that reduction or inhibition of the measured activity of at least 20%, 50%, 75%, 90% or 100%, or any number in between, may be preferred for particular applications.

The Compounds

As described in the Summary, the instant disclosure provides prodrugs of biologically active 1,3-dioxane moiety containing compounds, such as the various 1,3-dioxane compounds described in international application Serial No. PCT/US07/60724, filed Jan. 18, 2007. Prodrugs of the 1,3-dioxane compounds are of particular interest, as these compounds are useful as PPAR modulators, TP receptor antagonists and/or TS inhibitors. The prodrugs generally include such active 1,3-dioxane compounds in which one or more of the available carboxylic acid group, phenolic group, the hydroxyl group, or the primary or secondary amine group is masked with a progroup $R^p$ that metabolizes in vivo to yield the active 1,3-dioxane drug.

The 1,3-dioxane moiety has the formula (I):

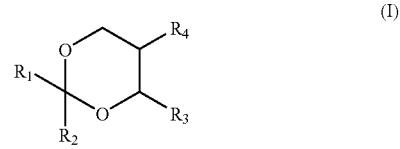

where $R_1$, $R_2$, $R_3$, and $R_4$ can be independently selected to be hydrogen, halo, haloalkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl or heteroaryl.

In particular, the 1,3-dioxane moiety has the structure of formula (II):

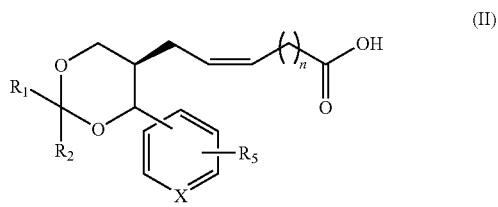

wherein $R_1$ can be hydrogen, halogen, cyano, hydroxyl, or alkyl; $R_2$ can be hydrogen, alkyl, alkenyl, aryl, heteroaryl, or a $C_{3\text{-}30}$ cyclic or heterocyclic ring optionally substituted with one or more substituent; X can be CH, or N; n can be 0, 1, 2, 3, 4, or 5; and $R_5$ can be H, OH, alkoxy, alkyl, or halogen. The substituent can be H, —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2O^-$, —$(CH_2)_{0\text{-}4}S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. The $C_{3\text{-}30}$ cyclic or heterocyclic ring can be unsubstituted, singly substituted or multiply substituted acenaphthene, benzothiophene, chromanone, indole, julolidine, naphthalene, quinoline, and the like.

The invention provides novel compounds containing the 2,4-diaryl-1,3-dioxane moiety in particular, and compositions comprising the compounds. In one aspect, the compounds of the invention have the formula (III):

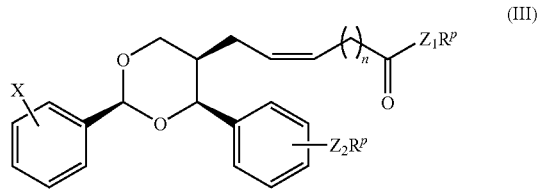

where X can be hydrogen, halogen, cyano, nitro, hydroxyl, haloalkyl, alkyl, or O—R where R is a lower alkyl group, such as methoxy, ethoxy, and the like; n can be 0, 1, 2, 3, 4, or 5; $Z_1$ and $Z_2$ are independently selected to be O, N, or S, and each $R^p$ is independently selected from H, lower alkyl, or a progroup. Those of skill in the art will appreciate that the compounds of the invention described herein may include functional groups that can be masked with progroups to create prodrugs. Such prodrugs are usually, but need not be, pharmacologically inactive until converted into their active drug form. In the prodrugs of the invention, any available functional moiety may be masked with a progroup to yield a prodrug. Myriad progroups suitable for masking such functional groups to yield promoieties that are cleavable under the desired conditions of use are known in the art.

The compounds of the invention that have a functional group that can be derivatized, such as the phenolic functional groups, the carboxylic functional group, the thiol functional group, and the like, can be used for the synthesis of prodrugs. It will be appreciated by one of skill in the art that the compounds of Formula III encompass both enantiomers, such as for example, shown below:

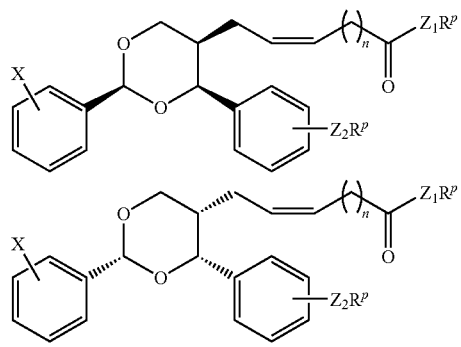

The nature of the progroup can vary, and will depend upon, among other factors, the desired water solubility of the prodrug, its intended mode of administration and/or its intended mechanism or site of metabolism to the active 2,4-diaryl-1,3-dioxane compound. For example, the progroup can be lipophilic or hydrophilic, where the lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc.

Groups capable of imparting prodrugs with these characteristics are known in the art, and are described, for example, in Ettmayer et al. (2004) J. Med. Chem. 47: 2393-2404. All of the various groups described in these references can be utilized in the prodrugs described herein.

The suitability of any particular progroup for a desired mode of administration can be confirmed in biochemical assays. For example, if a prodrug is to be administered by injection into a particular tissue or organ, and the identities of the various enzyme(s) expressed in the tissue or organ are known, the particular prodrug can be tested for metabolism in biochemical assays with the isolated enzyme(s). Alternatively, the particular prodrug can be tested for metabolism to the active 2,4-diaryl-1,3-dioxane compound with tissue and/or organ extracts. Using tissue and/or organ extracts can be of particular convenience when the identity(ies) of the enzymes expressed in the target tissues or organs are unknown, or in instances when the isolated enzymes are not conveniently available. Skilled artisans will be able to readily select progroups having metabolic properties (such as kinetics) suitable for particular applications using such in vitro tests. The specific prodrugs could also be tested for suitable metabolism in in vitro animal models.

The prodrugs or the invention are designed to overcome pharmaceutically and/or pharmacokinetically based problems associated with the parent drug molecule that would otherwise limit the clinical usefulness of the drug. The advantage of a prodrug lies in its physical properties, such as enhanced water solubility for parenteral administration at physiological pH compared to the parent drug, or it enhances absorption from the digestive tract, or it may enhance drug stability for long-term storage.

Exemplarity prodrugs of the compounds of the invention include:

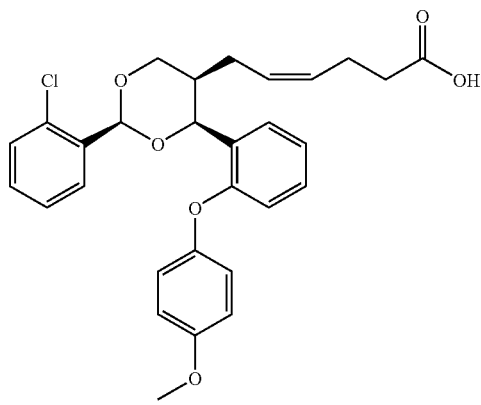

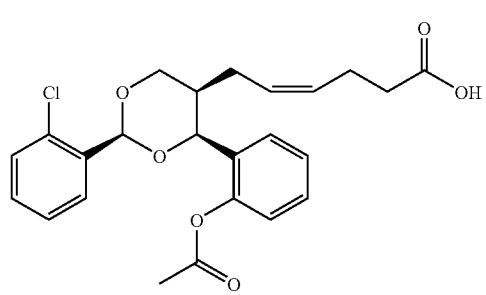

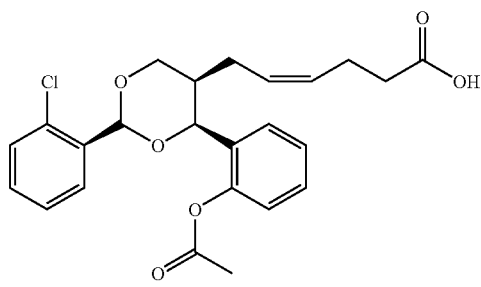

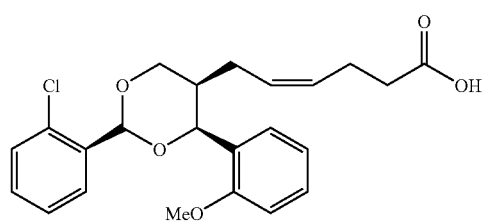

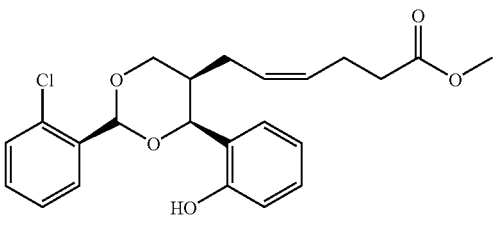

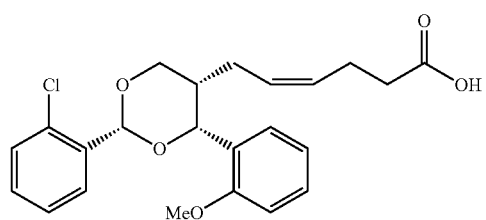

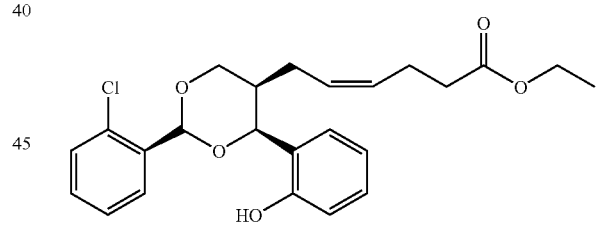

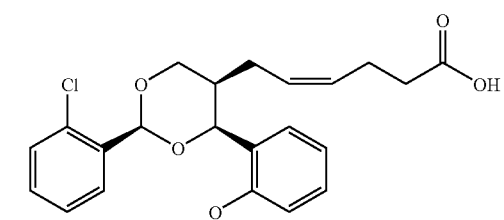

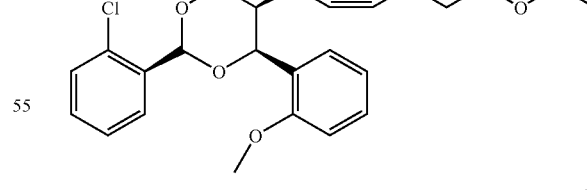

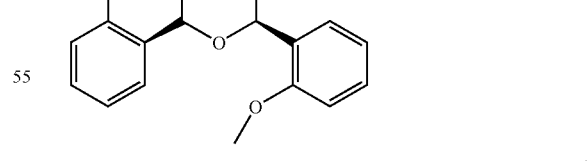

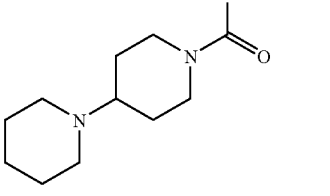

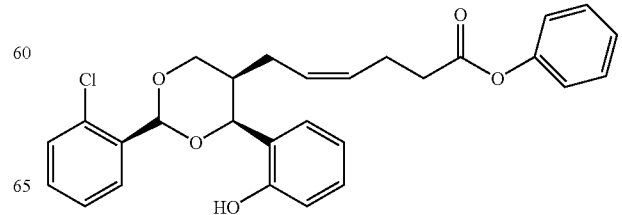

-continued

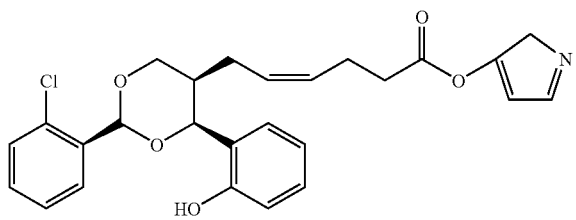

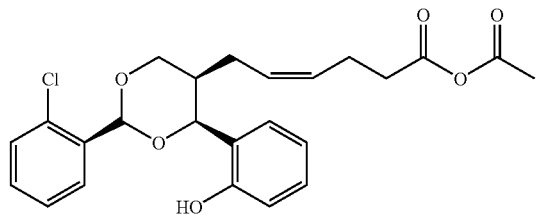

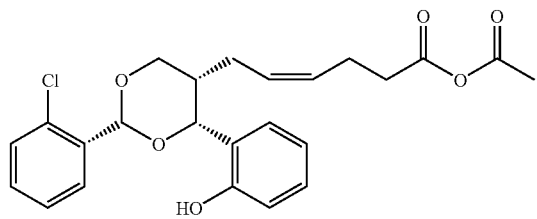

All of the various groups described in these references can be utilized in the prodrugs described herein. For example, when a compound of the present invention contains a carboxylic acid functional group, a prodrug can comprise an ester formed by the replacement of the hydrogen atom of the acid group with a group including, but not limited to, groups such as for example ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N (alkoxycarbonyl)amino)ethyl having from 4 to 10 carbon atoms, 3-phthalidyl, 4 crotonolactonyl, gamma-butyrolacton-4-yl, di-N,N—($C_1$-$C_2$)alkylamino($C_2$-$C_3$)alkyl, carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl. The prodrug may also be a compound wherein an —COOH group has reacted with a saccharide to form an ester, the saccharide preferably being a mono- or disaccharide, more preferably, a monosaccharide, even more preferably glycose. In particular, the phenol group can be converted to phosphate esters, alkyl esters, or derivatized using polyethylene glycol (PEG), alkyloxycarbonykloxymethyl (AOCOM), or as a sterically hindered alkoxycarbonyloxymethyl, as illustrated below.

PHOSPHATE ESTERS

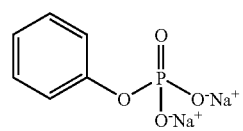 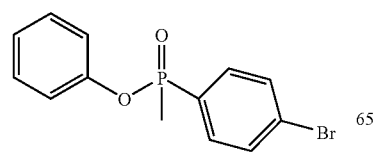

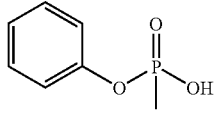

ALKYL ESTERS

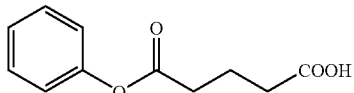

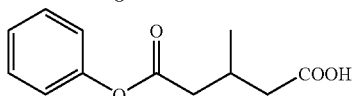

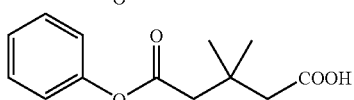

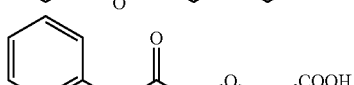

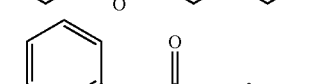

PEG DERIVATIVES

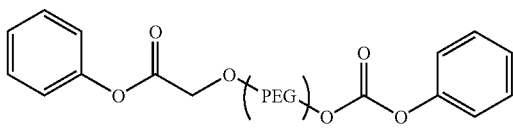

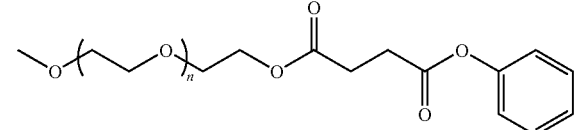

ALKYLOXYCARBONYKLOXYMETHYL (AOCOM) DERIVATIVES

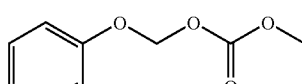

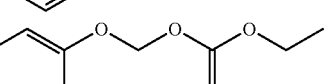

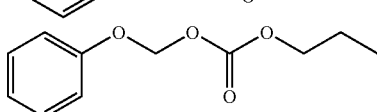

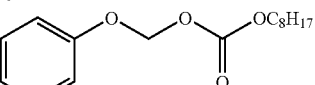

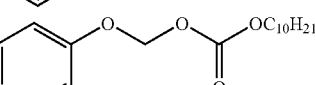

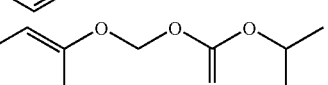

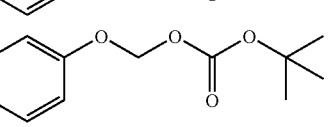

-continued
STERICALLY HINDERED ALKOXYCARBONYLOXYMETHYL DERIVATIVES

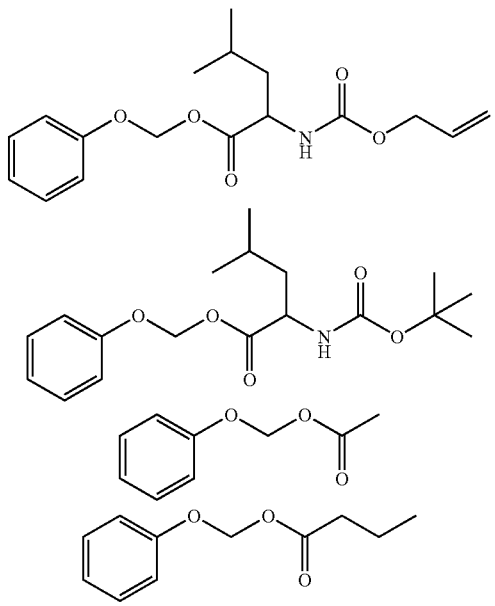

Methods of Synthesis

The compounds of the invention comprise 1,3-dioxane moiety, as described above. The compounds of the present invention, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTY 3$^{rd}$ Ed., Vols. A and B (Plenum 1992), and Green and Wuts, PROTECTIVE GROUPS IN ORGANIC SYNTHESIS 2$^{nd}$ Ed. (Wiley 1991). Starting materials useful for preparing compounds of the invention and intermediates thereof are commercially available, such as Aldrich Chemical Co. (Milwaukee, Wis.), Sigma Chemical Co. (St. Louis, Mo.), or Maybridge (Cornwall, England), or can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Alternatives to the reagents and/or protecting groups may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

The compounds and intermediates described herein can be synthesized via a variety of different synthetic routes using commercially available starting materials and/or starting materials prepared by conventional synthetic methods. Suitable exemplary methods that may be routinely used and/or adapted to synthesize active 1,3-dioxane compounds can be found in U.S. Pat. No. 4,895,962, and international application Serial No. PCT/US07/60724 filed on Jan. 18, 2007. The 1,3-dioxane compounds can further be used as starting materials to synthesize the prodrugs.

Thus, for example, the compounds of the can be synthesized using the reactions shown in Scheme 1 below:

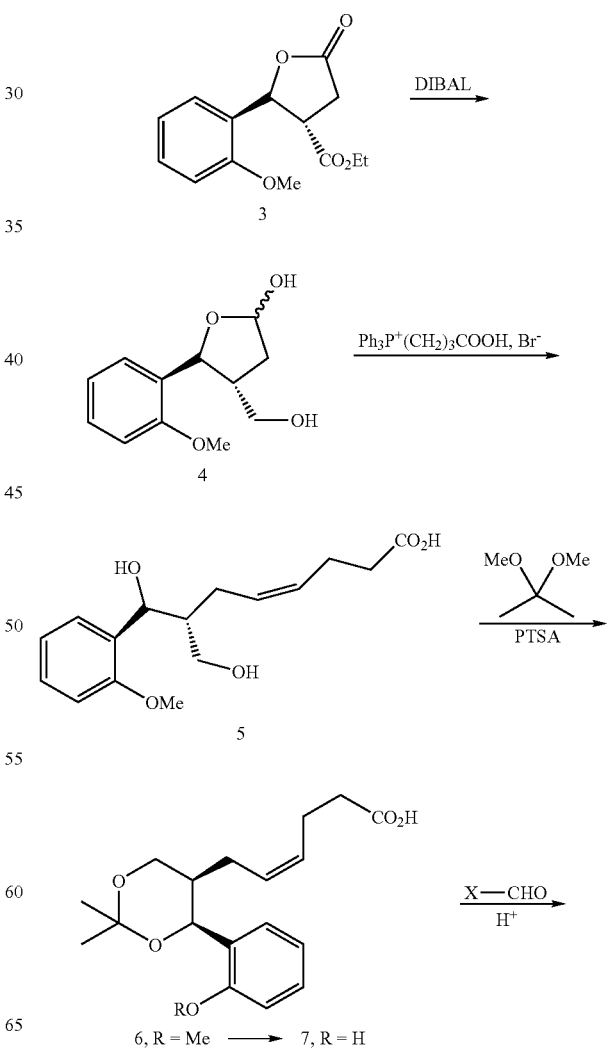

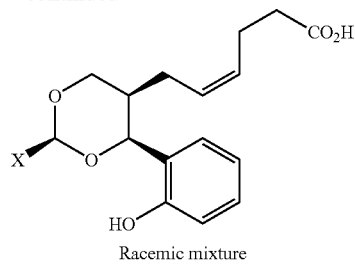

Racemic mixture

In addition, the synthetic procedures described herein can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

The compounds of the invention can also be made using the synthetic method of Scheme 2:

Scheme 2.

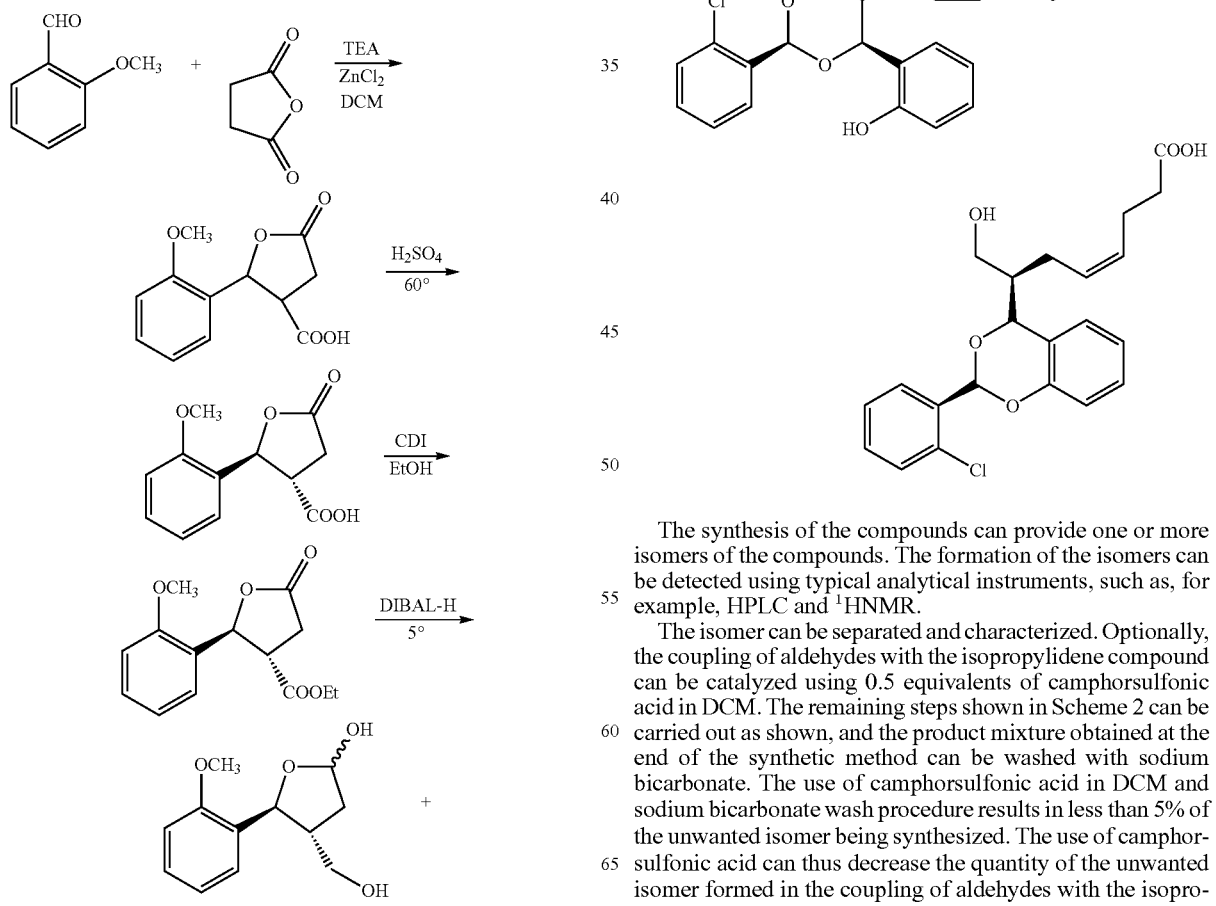

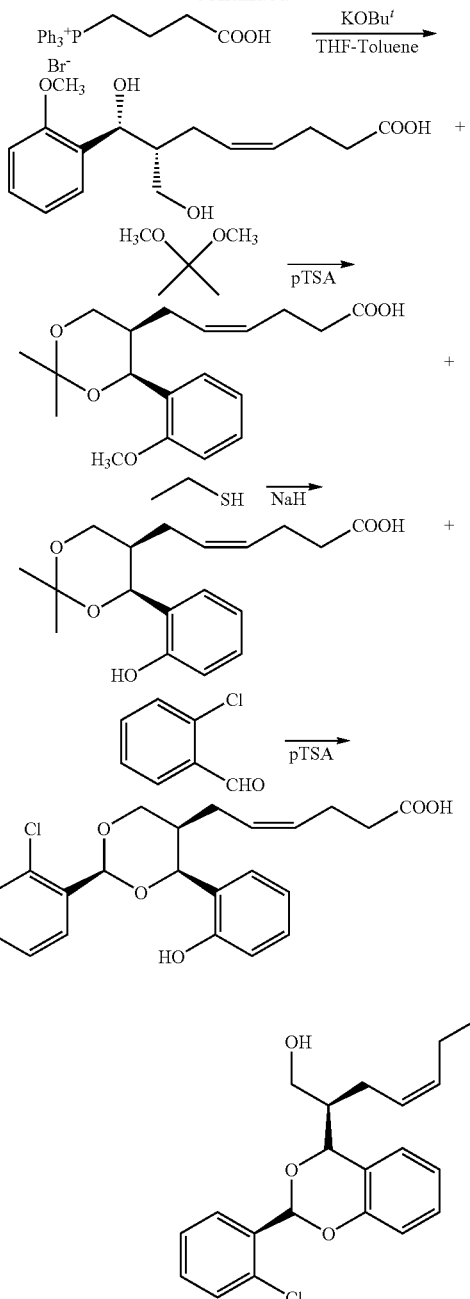

The synthesis of the compounds can provide one or more isomers of the compounds. The formation of the isomers can be detected using typical analytical instruments, such as, for example, HPLC and $^1$HNMR.

The isomer can be separated and characterized. Optionally, the coupling of aldehydes with the isopropylidene compound can be catalyzed using 0.5 equivalents of camphorsulfonic acid in DCM. The remaining steps shown in Scheme 2 can be carried out as shown, and the product mixture obtained at the end of the synthetic method can be washed with sodium bicarbonate. The use of camphorsulfonic acid in DCM and sodium bicarbonate wash procedure results in less than 5% of the unwanted isomer being synthesized. The use of camphorsulfonic acid can thus decrease the quantity of the unwanted isomer formed in the coupling of aldehydes with the isopropylidene compound.

Indications

Compounds of the present invention are useful for, but not limited to, the prevention or treatment of cancer and related diseases. The compounds of the invention have thromboxane A2 and/or PPAR modulatory activity. The compounds of the invention are useful in therapy for obesity, diabetes, cancer, inflammation, AIDS, metabolic syndrome, obesity, pre-diabetes, hypertension and dyslipidemia and the commonly associated disorders such as cardiovascular and hepatic disease agents.

The compounds of the invention are useful for treating or preventing a clinical condition that is a PPAR-mediated disease or condition in an individual in need thereof. The clinical condition can be diabetes, cancer, inflammation, AIDS, metabolic syndrome, obesity, pre-diabetes, hypertension and dyslipidemia.

The composition can be used for the treatment of clinical condition associated with thromboxane that can be myocardial infarction, thrombosis, thrombotic disorders, pulmonary hypertension, atherosclerosis, diabetic nephropathy, retinopathy, peripheral arterial disease, lower limb circulation, pulmonary embolism, thrombus formation, stent-triggered thrombus formation, stent-triggered hyperplasia, septic shock, preeclampsia, asthma, allergic rhinitis, tumour angiogenesis and metastasis Preferred compounds of the invention are any of the compounds described herein above that are PPAR modulators, in particular PPARgamma selective modulators (full or partial agonists or antagonists, preferably agonists), TP receptor antagonists or TS inhibitors, or compounds exhibiting two or more of these properties. Although not wishing to be bound by theory, the present inventors believe compounds that are TP receptor antagonists and TS inhibitors are particularly desirable as this leads to increased PGI2 levels which inhibits platelet aggregation and acts as a potent vasodilator.

Agonists and antagonists are characterized by their binding affinities, dictating potency/$EC_{50}$/$IC_{50}$ values, and by the level of activity, which is attained in the presence of saturating levels of the compounds, i.e. efficacy. A partial agonist/partial antagonist is also characterized by its binding affinity, and efficacy. Thus, a partial agonist/partial antagonist of PPAR is unable to fully activate the cognate PPAR and can in a competitive manner displace a full agonist from the receptor and thereby diminish the level of transactivation. Full and partial agonists of PPAR furthermore may recruit different complements of cofactors, and the nature of the cofactors recruited to a given PPAR subtype may profoundly influence the pattern of genes activated by a given agonist.

The ligand-binding pockets of the PPARs are large compared with other nuclear receptors, and this may in part explain the large variety of compounds that are able to bind to and activate the PPARs. There is a considerable overlap in ligand recognition between the three PPAR subtypes, and strictly speaking, no subtype specific ligand has yet been identified. However, several natural and synthetic ligands exhibit a great degree of selectivity, and the most selective ligands today differ by more than 3 orders of magnitude with regard to the concentration needed to activate the individual PPAR subtypes. In analogy with agonists for the steroid nuclear receptors, the term selective PPAR modulators (SP-PARMs) has been introduced (herein also referred to as "Partial agonists or antagonists"). This class of ligand comprises partial agonists/antagonists that upon binding to the PPAR(s) introduce different conformations leading to recruitment of different sets of coactivators. In principle, a SPPARM would be able to activate only a subset of PPAR target genes thereby possibly promoting specific expression of a desirable set of genes. The compounds according to the present invention are partial PPAR agonists.

PPAR modulating activity can be easily determined by any number of methods known in the art or adaptations thereof. For example, PPAR modulating activity may be determined by an in vitro transactivation assay known in the art, such as, for example, by using transactivation assay for determining PPARgamma modulating activity. It will be apparent to one of ordinary skill in the art that any number of possible constructs can be used, such as using different DNA binding domains to activate transcription or different reporter genes (for example, fluorescent proteins, beta-galactosidase, peroxidase, luciferase, or the like). It will also be apparent to one of ordinary skill in the art that depending on which PPAR activity it is desirable to determine, the construct preferably encodes said PPAR or a ligand binding domain thereof. Upon activation of PPAR (i.e., in the presence of a PPAR agonist or partial agonist), PPAR transactivates the reporter construct, optionally in a quantitative manner.

PPAR modulators may also be identified using a reporter gene comprising a first nucleic acid operably under control of a second nucleic acid comprising at least one PPRE. The first nucleic acid preferably encodes a reporter protein, such as a fluorescent protein, beta-galactosidase, peroxidase, luciferase, or the like. Said reporter construct should be inserted into a cell expressing one or more PPARs, such as PPARgamma and/or delta. PPAR agonists can thus be identified as compounds capable of activating transcription of the first nucleic acid.

According to a preferred embodiment, the compounds and compositions of the present invention are PPAR and/or PPAR LBD partial agonists, and more particularly, the compounds and compositions of the present invention are PPARgamma and/or PPARgamma LBD partial agonists. The term "PPAR LBD" refers to the ligand binding domain of PPAR. A drug that produces less than the possible maximal effect (i.e. the maximal effect produced by a full agonist, or reference molecule) is called a partial agonist.

In one embodiment it is preferred that the compounds of the invention are selective for activation of PPAR. In such an embodiment it is preferred that the compound does not significantly activate RxR and/or RxR LBD transactivation, preferably RxR transcription is less than 2 times background levels, such as less than 1.5 times background levels, for example approximately equal to or less than background level. RxR transactivation may be determined by an RxR transactivation assay. Background level is transactivation in the absence of an added ligand.

In addition, preferred PPAR modulators are PPAR modulators wherein administration of said PPAR modulator to an individual in a dosage in the range of 10 to 100 mg/kg, such as in the range of 30 to 70 mg/kg, for example in the range of 50 to 60 mg/kg, such as 53 mg/kg does not result in a significant increase in one or more, preferably at least 2, such as at least 3, for example all 4 of the following biological entities: Hematocrit, aspartate aminotransferase (AST), alanine aminotransferase (ALT) and alkaline phosphatases (ALP) in said individual. By "significant increase" is meant an increase of more than 30%, for example of more than 20%, such as of more than 10%, for example of more than 5%.

All aforementioned individuals in this section may be any individual, such as an individual in need of administration of a PPAR modulator, for example a human being suffering from one or more of the PPAR related clinical conditions mentioned herein elsewhere. However, the individual may also be a laboratory test animal, for example a mouse. All aforementioned decreases and increases in this section are in general determined in relation to the values obtained in similar individuals to which said PPAR modulator has not been administered.

The in vivo occurrence of undesirable side effects such as haemodilution, oedema, adipocyte differentiation, or obesity may be influenced by the cofactor recruitment profile of said compounds, for example using methods described in EP1267171. Thus, in one embodiment of the invention, preferred compounds are compounds which are predicted to have low in vivo occurrence of undesirable side effects.

In one embodiment of the invention the preferred compounds of the invention are capable of binding the thromboxane receptor (TP), such as capable of binding Thromboxane receptor in human recombinant HEK-293 cells. In particular, the compounds of the invention are capable of binding the thromboxane receptor with an $IC_{50}$ of less than 100 nM, more preferably less than 50 nM, even more preferably less than 30 nM, for example less than 20 nm, such as less than 10 nM, for example less than 5 nM, for example less than 1 nM are preferred. In addition, compounds of the invention capable of binding the thromboxane receptor with a Ki of less than 100 nM, more preferably less than 50 nM, even more preferably less than 20 nM, such as less than 10 nM, for example less than 5 nM, for example less than 1 nM are preferred. Preferably aforementioned $IC_{50}$ and Ki are determined by methods known in the art.

Preferred TP receptor modulators are TP receptor antagonists. The physiological function of TP receptors include the control of platelet aggregation, vasoconstriction and bronchoconstriction (see The IUPHAR compendium of receptor characterization and classification 1998, page 239, and The Sigma-RBI Handbook 5th edition, Prostanoid receptors, 2006, pages 138-140). Thus, the preferred PPAR/TP modulators according to the invention, which are antagonists of TP receptors are useful in treatment of a clinical condition characterized by one or more of increased platelet aggregation, increased vasoconstriction and increased bronchoconstriction, myocardial infarction, thrombosis, thrombotic disorders, pulmonary hypertension, atherosclerosis, IgA nephropathies, hepatorenal syndrome, diabetic nephropathy, retinopathy, diabetic retinopathy, peripheral arterial disease, lower limb circulation, pulmonary embolism, thrombus formation, hyperplasia, septic shock, preeclampsia, asthma, allergic rhinitis, tumour angiogenesis and metastasis, stent-triggered thrombus formation, stent induced restenosis and stent-triggered hyperplasia.

Preferred compounds of the invention are capable of inhibiting platelet aggregation. In particular, compounds capable of inhibiting platelet aggregation (that is, in conditions of increased platelet aggregation the compound would normalize platelet aggregation) by at least 20%, preferably at least 40%, more preferably at least 50%, yet more preferably at least 80%, for example at least 90%, such as at least 94%, for example at least 95%, such as at least 97%, for example approximately 100%, such as 100% at a concentration of in the range of 0.01 to 100 μM, preferably in the range of 1 to 30 μM, for example approximately 1 μM, such as approximately 8 μM, for example approximately 16 μM, such as approximately 30 μM, for example 1 μM, such as 8 μM, for example 16 μM or such as 30 μM.

Besides being useful for human treatment, these compounds are also useful for veterinary treatment of companion animals, exotic animals and farm animals, including mammals, rodents, and the like. More preferred animals include horses, dogs, and cats. As used herein, the compounds of the present invention include the pharmaceutically acceptable derivatives thereof.

Clinical Conditions

The present invention relates to methods of treatment of clinical conditions comprising administration of above-mentioned compounds (preferably any of the PPAR agonists, TP receptor antagonists, TS inhibitors mentioned above, as well as to uses of said compounds for preparation of a medicament for treatment of a clinical condition.

The PPAR modulators described herein above may be employed in weight control. Thus, the clinical condition may in one embodiment be an eating disorder such as anorexia nervosa (also abbreviated "anorexia" herein) or bulimia.

In one preferred embodiment, the invention relates to methods for treating insulin resistance by administering any of the compounds described herein above. The invention also relates to use of any of said compounds for preparation of a medicament for the treatment of insulin resistance. In addition, the invention relates to methods for increasing insulin sensitivity by administration of said compounds, as well as to use of said compounds for the preparation of a medicament for increasing insulin sensitivity. Acute and transient disorders in insulin sensitivity, such as those that may occur following trauma, surgery, or myocardial infarction, may be treated as taught herein.

Insulin resistance is involved in a number of clinical conditions. Insulin resistance is manifested by the diminished ability of insulin to exert its biological action across a broad range of concentrations. During early stages of insulin resistance, the body secretes abnormally high amounts of insulin to compensate for this defect. Even though blood insulin levels are chronically high, the impaired metabolic response of active muscle cells to insulin make them unable to take up glucose effectively. It is now increasingly being recognized that insulin resistance and resulting hyperinsulinemia may contribute to several clinical conditions, for example to the metabolic syndrome (also designated syndrome X). The metabolic syndrome is characterized by a first insulin-resistant stage which causes hyperinsulinemia, dyslipidemia and reduced glucose tolerance. Patients with the metabolic syndrome have been shown to be at an increased risk of developing cardiovascular disease and/or type II diabetes and may be treated with the compounds of the invention.

Insulin resistance also has a negative effect on lipid production, contributing to increasing VLDL (very low-density lipoprotein), LDL (low-density lipoprotein), and triglyceride levels in the bloodstream and decreasing HDL (high-density lipoprotein). This can lead to fatty plaque deposits in the arteries which, over time, can lead to atherosclerosis. Thus, the clinical condition according to the present invention may be hyperlipidemia, such as familial hyperlipidemia. Preferably, hyperlipidemia is characterized by hypercholesterolemia and/or hypertriglyceridemia. The clinical condition may also include dyslipidemia and diabetic dyslipidemia. The compounds included herein may be utilized to lower serum triglyceride levels or raise the plasma level of HDL.

Insulin resistance may lead to excessive insulin and glucose levels in the blood. Excess insulin may increase sodium retention by the kidneys, thus the methods of the invention may be employed for decreasing sodium retention by the kidneys. Elevated glucose levels may damage blood vessels and kidneys. Thus, the compounds of the invention may be employed to prevent damage to blood vessels and kidneys.

In another embodiment of the invention, the clinical condition is an inflammatory disorder mediated by PPARgamma. By the term "mediated by PPARgamma," it should be understood that PPARgamma plays a role in the manifestation of the condition. For example, PPARgamma is considered not to play a role in inflammation associated with neutrophil activation, such as acute inflammations. Although not wishing to be bound by theory, agonists of PPARgamma may be effective anti-inflammatory drugs by directly associating with and inhibiting NFκB-mediated transcription and thus modulating various inflammatory reactions, such as, for example, the enzyme paths of inducible nitrous oxide synthase (NOS) and cyclooxygenase-2 (COX-2) (Pineda-Torra, I. et al., 1999, Curr. Opinion in Lipidology, 10, 151-9).

The inflammatory disorder may be acute or chronic, such as ocular inflammation (J Biol Chem. 2000 Jan. 28; 275(4): 2837-44) or dry eye disease (J Ocul Pharmacol Ther. 2003 December; 19(6):579-87), for example. Illustrative examples of chronic inflammatory disorder include inflammatory bowel disease, ulcerative colitis, or Crohn's disease. The chronic inflammatory disorder may also be arthritis, notably rheumatoid arthritis and polyarthritis. The chronic inflammatory disorder could also be an inflammatory skin disease, notably acne vulgaris, atopic dermatitis, cutaneous disorders with barrier dysfunction, cutaneous effects of aging or psoriasis, in particular psoriasis. The chronic inflammatory disorder may also be an inflammatory neurodegenerative disease, such as multiple sclerosis or Alzheimer's disease. The clinical condition may also be gastrointestinal diseases and renal diseases, including glomerulonephritis, glomerulosclerosis, nephritic syndrome, and hypertensive nephrosclerosis.

In another embodiment of the invention the clinical condition is a cancer responsive to activation of PPARgamma. Thus, the clinical condition may for example be a disorder characterized by aberrant cell growth of PPAR-responsive cells such as hyperplastic or neoplastic disorders arising in adipose tissue, such as adipose cell tumors, e.g., lipomas, fibrolipomas, lipoblastomas, lipomatosis, hibemomas, hemangiomas, and/or liposarcomas. Furthermore, certain cancers of prostate, stomach, lung and pancreas have been demonstrated to be responsive to treatment with PPARgamma agonists. In particular, certain liposarcomas, prostate cancers, multiple myelomas, and pancreatic cancers have been shown to be responsive to activation of PPARgamma, whereas at least some colorectal and breast cancers are not responsive (Rumi et al., 2004, Curr. Med. Chem. Anti-Canc Agents, 4:465-77). Other studies have demonstrated that other breast and colon cancers are responsive to PPAR agonists, as well as neuroblastoma and bladder cancers. The use of PPAR ligands for treatment of cancers was reviewed by Levy Kopelovich, 2002, Molecular Cancer Therapeutics, 357.

However, even though certain types of cancer may be responsive to activation with PPARgamma, all cancers of a given type may not be responsive. In particular, loss-of-function mutations of PPARgamma frequently occur in cancer and such cancers will in general not be responsive. Thus it is preferred that the cancer expresses functional PPARgamma.

The clinical condition may also be an infection, such as a viral infection, notably AIDS or infection by HIV or infection by the hepatitis C virus. In addition, the PPAR ligands of the invention may be useful for improving cognitive functions in neurologic diseases or in dementia or for treating polycystic ovarian syndrome or for preventing and treating bone loss, e.g., osteoporosis.

The clinical condition may also be a liver disease, notably infection by the hepatitis C virus, or fatty liver, liver inflammation, liver lesions, liver cirrhosis, non-alcoholic steatohepatitis, or post-hepatic cancer, whether or not associated with a hepatitis C virus infection, but preferably responsive to PPAR modulation. The clinical condition may also be Marfan syndrome.

Although much of the description has related to PPARgamma, the compounds and methods of the invention are not limited to the modulation of PPARgamma. Indeed, it will be apparent to the artisan that other PPAR subtypes play an important role in disease. In addition it is apparent to the skilled artisan that also the thromboxane receptor plays an important role in PPAR associated diseases. For example, PPARdelta has been associated with lipid metabolism disorders and wound healing, in particular epidermal wound healing (Soon Tan et al., 2004, Expert Opinion in Molecular Targets, 39). Thus, the clinical condition may also be wound healing, including epidermal wound healing.

The invention also relates to use of the compounds of the invention (preferably any of the PPAR modulators described above for preparation of a medicament for the simultaneous treatment and/or prevention of obesity and diabetes. Within this embodiment, diabetes is preferably diabetes type II or an individual at risk of acquiring diabetes, for example, an individual suffering from the metabolic syndrome described herein above. Said individual at risk of getting obese, may, for example, be an individual under medical treatment with an anti-diabetic compound having the side-effect of weight gain.

The invention also relates to use of any of the compounds described above, and preferred compounds referred to herein, for the preparation of a medicament for treatment or prevention, preferably treatment of a clinical condition associated with thromboxane in an individual in need thereof. The clinical condition may be a clinical condition characterized by increased platelet aggregation, vasoconstriction and/or bronchioconstriction. The clinical condition may, for example, be selected from the group consisting of myocardial infarction, thrombosis, thrombotic disorders, stent triggered thrombus formation, stent induced restenosis, stent-triggered hyperplasia, pulmonary hypertension, atherosclerosis, familial hypercholesterolemia, Kawasaki disease, ventricular septal defects, IgA nephropathies, hepatorenal syndrome, hepatic fibrosis, diabetic nephropathy, retinopathy, diabetic retinopathy, peripheral arterial disease, lower limb circulation, pulmonary embolism, thrombus formation, hyperplasia, septic shock, preeclampsia, asthma, rhinitis, allergic rhinitis, tumour angiogenesis and metastasis. The clinical condition related to thromboxane (TP) may also be selected from the group consisting of myocardial infarction, angina, unstable angina, stroke, transient cerebral vascular ischemia, migraine, atheroschlerosis, microangiopathy, hypertension, blood clotting defects, warfarin sparing situations (e.g., prior to surgery), pulmonary embolism, bronchial asthma, bronchitis, chronic bronchitis, pneumonia, dyspnoea and emphysema. In one preferred embodiment the clinical condition is selected from the group consisting of thrombosis, pulmonary hypertension, diabetic nephropathy, retardation of renal damage (in particular in diabetic patients), retinopathy, peripheral arterial disease, lower limb circulation, thrombus formation, stent triggered thrombus formation, stent induced restenosis, stent-triggered hyperplasia, hyperplasia, septic shock, preeclampsia, rhinitis, allergic rhinitis, tumour angiogenesis and metastasis, preferably from the group consisting of thrombosis, pulmonary hypertension, diabetic nephropathy, retinopathy, peripheral arterial disease, lower limb circulation, thrombus formation and hyperplasia. Individuals resistant to aspirin, clopidrogel, warfarin and other similar medicaments acting by different mechanisms are particularly benefited by treatment with the compounds described herein. Furthermore, the individual may be any individual suffering from or at risk of contracting any of the aforementioned clinical conditions associated with TP, preferably the individual is a human being suffering from or at risk of contracting any of the aforementioned clinical conditions associated with TP, even more preferably said individual is a human being suffering from diabetes in addition to suffering from or being at risk of contracting any of the aforementioned clinical conditions associated with TP.

In one embodiment the invention relates to treatment of thrombosis in an individual, who has already thrombosis, suffered one or more thrombotic events, or is suffering from one or more thrombotic events, said method comprising administration of any of the compounds described above to said individual The invention also relates to use of any of the specific compounds described above for the preparation of a medicament for treatment or prevention of a clinical condition. The clinical condition may be selected from the group consisting of the metabolic syndrome, dislipidemia, obesity, diabetes mellitus, insulin resistance or any of the conditions related to insulin resistance described above, hypertension, cardiovascular disease, coronary artery restenosis, autoimmune diseases (such as asthmas, multiple sclerosis, psoriasis, topical dermatitis, and ulcerative colitis), cancer, inflammation, wound healing, lipid metabolism disorders, liver disease (such as infection by the hepatitis C virus, or fatty liver, liver inflammation, liver lesions, liver cirrhosis or post-hepatic cancer whether or not associated with a hepatitis C virus infection), gastrointestinal or renal disease (such as glomerulonephritis, glomerulosclerosis, nephritic syndrome, or hypertensive nephrosclerosis), infection (in particular viral infection), cognitive function disorders (such as neurologic disorders or dementia), polycystic ovarian syndrome, bone loss (such as osteoporosis) and AIDS.

Cancer may be any cancer, for example any of the following: carcinomas, sarcomas, osteosarcoma, leukemias, and lymphomas; tumor angiogenesis and metastasis; skeletal dysplasia; hepatic disorders; and hematopoietic and/or myeloproliferative disorders. Exemplary disorders include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma. Preferably, the cancer is one of the above-mentioned cancers responsive to activation of PPARgamma.

Cardiovascular diseases may, for example, be atherogenesis, atherosclerosis or atherosclerotic disorders, vascular restinosis, cardiomyopathy, or myocardial fibrosis or any of the cardiovascular diseases mentioned above.

The inflammation may be, for example, a chronic inflammation, preferably any of the chronic inflammations mentioned herein above.

Diabetes mellitus refers to a disease process derived from multiple causative factors and characterized by elevated levels of glucose in blood, or hyperglycemia. Uncontrolled hyperglycemia is associated with increased and premature morbidity and mortality. At least two types of diabetes mellitus have been identified: (i) Type I diabetes, or Insulin Dependent Diabetes Mellitus (IDDM), which is the result of a complete lack of insulin, the hormone that regulates glucose utilization under normal physiological conditions, and (ii) the Type II diabetes, or Non Insulin Dependent Diabetes Mellitus (NIDDM). NIDDM is a complex disease derived from multiple causative factors, which can be addressed in some cases by increasing circulating insulin levels.

Uses and Administration

The compounds of the invention and/or compositions thereof find particular use in the treatment and/or prevention diseases in animals and humans caused by thromboxane A2 (TP) and/or PPAR. When used in this context, the compounds may be administered per se, but are typically formulated and administered in the form of a pharmaceutical composition. The exact composition will depend upon, among other things, the method of administration and will be apparent to those of skill in the art. A wide variety of suitable pharmaceutical compositions are described, for example, in *Remington's Pharmaceutical Sciences*, 20$^{th}$ ed., 2001).

By pharmaceutically acceptable carrier as used herein is meant one or more compatible solid or liquid delivery systems have innocuous physiological reactions when administered to a subject. Some examples include but are not limited to starches, sugars, cellulose and its derivatives, powdered tragacanth, malt, gelatin, collagen, talc, stearic acids, magnesium stearate, calcium sulfate, vegetable oils, polyols, agar, alginic acids, pyrogen free water, isotonic saline, phosphate buffer, and other suitable non-toxic substances used in pharmaceutical formulations. Other excipients such as wetting agents and lubricants, tableting agents, stabilizers, anti-oxidants, and preservatives are also contemplated.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

Formulations suitable for oral administration can consist of (a) liquid solutions, such as an effective amount of the active compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are the preferred methods of administration. A specific example of a suitable solution formulation may comprise from about 0.5-100 mg/ml compound and about 1000 mg/ml propylene glycol in water. Another specific example of a suitable solution formulation may comprise from about 0.5-100 mg/ml compound and from about 800-1000 mg/ml polyethylene glycol 400 (PEG 400) in water.

A specific example of a suitable suspension formulation may include from about 0.5-30 mg/ml compound and one or more excipients selected from the group consisting of: about 200 mg/ml ethanol, about 1000 mg/ml vegetable oil (e.g., corn oil), about 600-1000 mg/ml fruit juice (e.g., grapefruit juice), about 400-800 mg/ml milk, about 0.1 mg/ml carboxymethylcellulose (or microcrystalline cellulose), about 0.5 mg/ml benzyl alcohol (or a combination of benzyl alcohol and benzalkonium chloride) and about 40-50 mM buffer, pH 7 (e.g., phosphate buffer, acetate buffer or citrate buffer or, alternatively 5% dextrose may be used in place of the buffer) in water.

A specific example of a suitable liposome suspension formulation may comprise from about 0.5-30 mg/ml compound, about 100-200 mg/ml lecithin (or other phospholipid or mixture of phospholipids) and optionally about 5 mg/ml cholesterol in water.

The formulations of compounds can be presented in unit-dose or multi-dose sealed containers, such as ampules and vials. Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below.

In therapeutic use, the compounds utilized in the pharmaceutical method of the invention are administered to patients at dosage levels suitable to achieve therapeutic benefit. By therapeutic benefit is meant that the administration of compound leads to a beneficial effect in the patient over time.

Initial dosages suitable for administration to humans may be determined from in vitro assays or animal models. For example, an initial dosage may be formulated to achieve a serum concentration that includes the $IC_{50}$ of the particular compound being administered, as measured in an in vitro assay. Alternatively, an initial dosage for humans may be based upon dosages found to be effective in animal models of the disease. As one example, the initial dosage may be in the range of about 0.01 mg/kg/day to about 200 mg/kg/day, or about 0.1 mg/kg/day to about 100 mg/kg/day, or about 1 mg/kg/day to about 50 mg/kg/day, or about 10 mg/kg/day to about 50 mg/kg/day, can also be used. The dosages, however, may be varied depending upon the requirements of the patient, the severity of the condition being treated, and the compound being employed. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

Combination Therapy

In certain embodiments of the present invention, the compounds of the invention and/or compositions thereof can be used in combination therapy with at least one other therapeutic agent. A compound of the invention and/or composition thereof and the therapeutic agent can act additively or, more preferably, synergistically.

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

Co-administration of a compound of the present invention and another pharmaceutical agent is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Combination therapy includes administration of a single pharmaceutical dosage composition, which contains a compound of the present invention and one or more additional active agents, as well as administration of a compound of the present invention and each active agent in its own separate pharmaceutical dosage. For example, a compound of the present invention and an insulin secretogogue such as sulfonylureas, thiazolidinediones, biguanides, meglitinides, insulin or β-glucosidase inhibitors can be administered to the patient together in a single oral dosage composition such as a capsule or tablet, or each agent administered in separate oral dosages. Where separate dosages are used, a compound of the present invention and one or more additional active agents can be administered at essentially the same time, i.e., concurrently or at separately staggered times, i.e., sequentially; combination therapy is understood to include all these regimens.

Alternatively, the present compounds can also be used in co-therapies with other anti-neoplastic agents, such as other kinase inhibitors including p38 inhibitors and CDK inhibitors, TNF inhibitors, metallomatrix proteases inhibitors (MMP), EGFR inhibitors such as Iressa, KDR inhibitors, COX-2 inhibitors including celecoxib, rofecoxib, parecoxib, valdecoxib, and etoricoxib, NSAID's, SOD mimics or αvβ3 inhibitors.

EXAMPLES

The following examples are provided by way of illustration only and not by way of limitation. Those of skill in the art will readily recognize a variety of noncritical parameters that could be changed or modified to yield essentially similar results.

The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

General Synthesis of the Compounds

A general synthetic scheme for the componds is shown below:

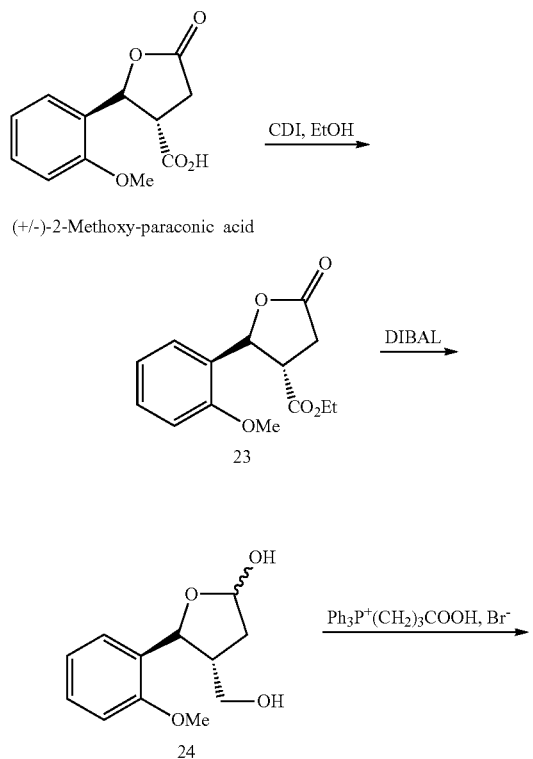

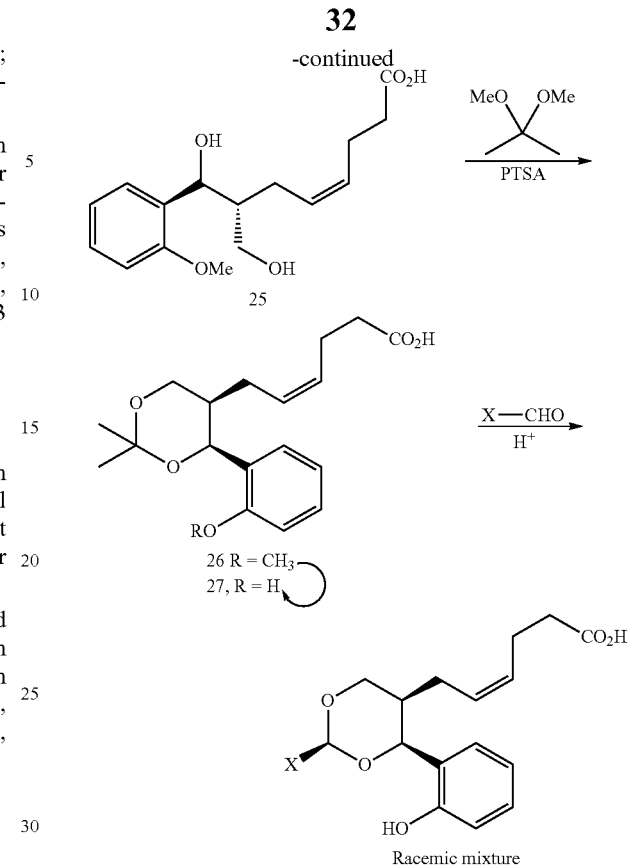

Esterification of Methoxy-Paraconic Acid 193 g of methoxy-paraconic acid was dissolved in 600 mL of THF, then CDI (145 g, 899 mmol, 1.1 eq) was added at room temperature over a 10 min period. Absolute ethanol 65 mL (or methanol to make the methyl ester) was added and the reaction mixture was stirred for about 120 min to give 188 g of compound 23. (Yield 87%).

Reduction of Racemic Methoxy-Paraconic Acid, Ethyl Ester 105 g of compound 23 (397 mmol) was dissolved in 700 mL of toluene at 5° C.

Then 3 eq. DIBAL-H (1.19 mol, 1.19 L 1M solution) was added, the reaction mixture was stirred for 60 min at room temperature and quenched with methanol. The product compound 24 recrystallized as an oily residue from chloroform/hexanes. Yield: 53 g (237 mmol, 59%).

Wittig Reaction Employing Racemic Lactol-Synthesis of Racemic Diol 191 g carboxypropyltriphenylphosphonium bromide, anhydrous toluene 1000 mL and 100 g potassium t-butoxide were mixed at 80° C. for 30 min. The mixture was cooled to room temperature, and purified racemic lactol 24 (25 g, 114.5 mmol) pre-dissolved in anhydrous THF 180 mL was added. The mixture was stirred for 60 min to provide the product 25. Yield: 26 g (88.3 mmol, 79%).

Conversion of Racemic Diol into Racemic Acetonide

The diol 25 26 g (88 mmol) was dissolved in 260 mL dimethoxypropane and 26 mg p-TsOH was added. The mixture was allowed to stir at ambient temperature overnight. The product acetonide 26 was purified by stirring with hexane. Yield: 25 g (75 mmol), 85%.

De-Methylation of Racemic Acetonide

Ethanethiol 16.7 g was added to a mixture of NaH 21.5 g in 375 mL DMPU. The mixture was heated to 80° C., and allowed to cool to ambient temperature. Then, racemic acetonide (26, 15 g) dissolved in 75 mL DMPU was added to the suspension of EtSH/NaH. The mixture was heated at 130° C. for 2 h. The reaction mixture was then poured into ice-water and extracted with DCM. Yield: 16.5 g (crude).

Preparation of Racemic Product

De-methylated racemic acetonide 27 8.97 g, 28 mmol mixed with 15 mL 2-chlorobenzaldehyde, 0.5 g of p-TsOH, and 60 mL of toluene stirred for 24 h and evaporated. Yield: 6.5 g (16.7 mmol, 59%)

Example 2

Synthesis of Prodrug 1

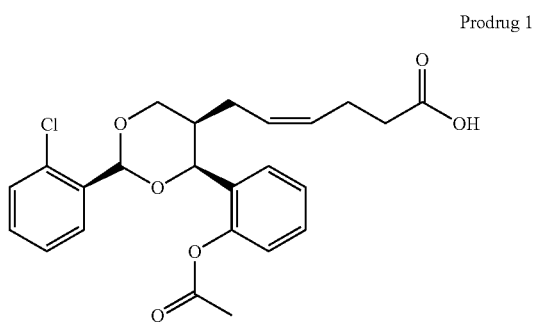

Prodrug 1

Prodrug 1 was synthesized using the acid synthesized in Example 1 as the starting compound. The acid was dissolved in dichloromethane (90 mg in 5 mL), the solution was cooled to 4° C., and then 4-dimethylaminopyridine (DMAP, 5 mg), pyridine (2.5 eq) and acetic anhydride (1.1 eq) were added. After 15 minutes, the temperature was raised to 20° C., and the reaction mixture was stirred further for 3 hours. LC-MS analysis of the crude revealed the disappearance of the starting material, as well as the presence of a new peak, with the expected molecular weight. DCM was removed under vacuum and the crude mass was purified by preparative RP-HPLC (on a 35 to 90% B vs A gradient over 8 minutes at a 10 ml/min flow rate using a Waters XBridge OBD C18, 5 μm, 19×100 mm, preparative column).

Lyophilisation yielded a white sticky solid (45 mg, 45%). Retention time is 6.67 minutes (on a 35 to 90% B vs A gradient over 10 minutes at a 1 ml/min flow rate, using a Waters XBridge C18, 5 μm, 4.6×100 mm, analytical column) and purity is higher than 98%. MS analysis: m/z=467.1 (M+Na$^+$)

Example 3

Synthesis of Prodrug 2

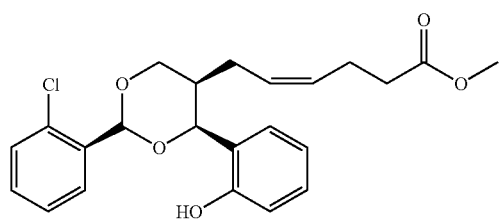

Prodrug 2

Prodrug 2 was synthesized using the acid synthesized in Example 1 as the starting compound. The acid was dissolved in dichloromethane (140 mg in 5 mL), the solution was cooled to 4° C., and then dicyclocarbodiimide (DCC, 1.1 eq) and methanol (2 ml) were added. After 15 minutes, the temperature was raised to 20° C., and the reaction mixture was stirred further for 2 hours. LC-MS analysis of the crude revealed the disappearance of the starting material, as well as the presence of a new peak, with the expected molecular weight. Solvents were removed under vacuum and the crude mass was purified by preparative RP-HPLC (on a 50 to 90% B vs A gradient over 9 minutes at a 10 ml/min flow rate using a Waters XBridge OBD C18, 5 μm, 19×100 mm, preparative column).

Lyophilisation yielded a white solid (89 mg, 61%). Retention time is 7.74 minutes (on a 35 to 90% B vs A gradient over 10 minutes at a 1 ml/min flow rate, using a Waters XBridge C18, 5 μm, 4.6×100 mm, analytical column) and purity is higher than 98%.

MS analysis: m/z=439.1 (M+Na$^+$)

Example 4

Synthesis of Prodrug 3

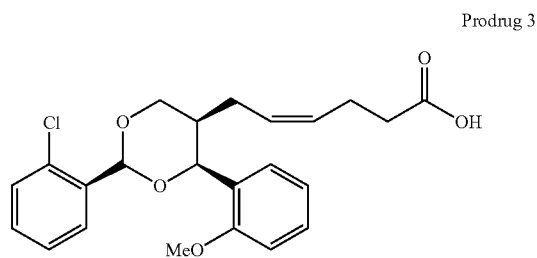

Prodrug 3

Prodrug 3 was synthesized using the synthesis described in Example 1 and by omitting the final deprotection step (removal of the phenolic methyl ether group by thioalkanes) before coupling of 2-chlorobenzaldehyde. The compound can, for example, be purified by preparative RP-HPLC (on a 50 to 90% B vs A gradient over 9 minutes at a 10 ml/min flow rate using a Waters XBridge OBD C18, 5 μm, 19×100 mm, preparative column).

Lyophilisation yielded a white solid. Retention time is 6.65 minutes (on a 50 to 90% B vs A gradient over 10 minutes at a 1 ml/min flow rate, using a Waters XBridge C18, 5 μm, 4.6×100 mm, analytical column) and purity is higher than 98%.

MS analysis: m/z=419.1 (M+H$^+$)

HPLC solvents: A is water with 0.1% formic acid, B is acetonitrile with 0.1% formic acid.

Example 5

Improved Exposure to Drug Through Using Pro-Drug

This Example illustrates the improved exposure in vivo to the active component of the prodrug upon administration of a prodrug.

Briefly, male Wistar rats were allocated into groups for doses as indicated in Table 1. Animals were fasted overnight before dosing p.o. (gavage or capsule) or by bolus intravenous application. Blood samples (approx. 0.15 ml) were taken at different time points into heparinized tubes by automated blood sampling. Plasma was prepared and stored frozen until bioanalysis.

Bioanalytical Sample Preparation
to an aliquot of 10 μL plasma 30 μL ACN/EtOH (50/50, v/v) are added
vortex
20 min 14000 rpm approx. 8° C.
Supernatant transfer in HPLC vial
Liquid Chromatography

| Column: ZORBAX 5 μm, Eclipse XDB-C18, 2.1 × 50 mm | | | | | | |
|---|---|---|---|---|---|---|
| | Time [min] | | | | | |
| | 0.0 | 0.4 | 1.0 | 2.5 | 2.6 | 3.0 |
| Phase A [%] | 80 | 80 | 5 | 5 | 80 | 80 |
| Phase B [%] | 20 | 20 | 95 | 95 | 20 | 20 |
| Flow rate [μl/min] | 400 | 400 | 400 | 400 | 400 | 400 | mobile phases:
phase A water
phase B ACN

Analytical Pump:
Valve Switching:
From 1 to 2.5 minutes to the electrospray source (will be adjusted if required)

| Injection volume: | 10 μl in a 5 μl sample loop |
|---|---|
| Column temperature: | RT |

The samples were analyzed by mass spectroscopy using ESI (negative ion mode) as the ionization mode.
Selected Reaction Monitoring:

| Analyte | Parent ion mass [Th] | Product ion mass [Th] | Width [Th] | Scan time [s] | Collision energy [eV] |
|---|---|---|---|---|---|
| Drug | 401.2 | 187.1 | 0.1 | 0.05 | 20 |
| Prodrug 3 | 415.1 | 245.1 | 0.1 | 0.05 | 20 |

Autosampler
Wash 1: EtOH/water, 50/50 (v/v)
Wash 2: 2-Propanol/ACN/MeOH, 1/1/1 (v/v/v)
Non-Compartmental Analysis (NCA)

The quantitatively measured plasma concentration-time data were subjected to non-compartmental analysis (NCA) using the PCModfit program (version 3.00) for Windows® running with Excel 2003 (http://home2.btconnect.com/Gamms/PCModfit/; Allen, G. D. 'Modfit: a pharmacokinetics computer program' Biopharm. and Drug Disp., Vol. 11, 477-498, 1990). The points selected in each profile for half-life estimation using numerical analysis, where possible, corresponded to the final linear phase as visually assessed from ln(concentration) vs. time plots. The terminal elimination rate constant ($\lambda_z$) for each profile was numerically estimated using iteratively re-weighted non-linear least squares analysis with a weighting factor of $1/\hat{C}^2$. The area under the concentration-time curve to the last actual time point ($AUC_{0-t}$) and infinity ($AUC_{0-\infty}$) for each data set were estimated using a linear (ascending) trapezoidal method. The extrapolated area to infinity ($AUC_{0-\infty}$) was estimated, where possible, using $AUC_{0-t}$ and the predicted value ($\hat{C}_n$) at the last time point for each profile.

The equations used for the area under curve calculations are shown for information.

$$\text{Linear trapezoidal: } AUC_{0-t} = \sum_{i=1}^{n-1} \frac{(t_{i+1} - t_i)(C_{i+1} + C_i)}{2}$$

$$\text{Extrapolation to infinity: } AUC_{0-\infty} = AUC_{0-t} + \frac{\hat{C}_n}{\lambda_z}$$

The $C_i$ values correspond to the actual concentrations of drug at time $t_i$ for n data points.

The $C_0$ value was extrapolated using the first 4 time points.
The data is shown below in Table 1.

TABLE 1

| Compound | Tmax (min) | Cmax (ng/ml)/ Dose (mg/kg) | Lin-AUC (0-∞) (ng•min/ml)/ Dose (mg/kg) | T-Last (h) | Terminal Half-life elimination, t½z (min) |
|---|---|---|---|---|---|
| [structure: 2-Cl-phenyl dioxane with 2-HO-phenyl substituent and CH2-CH=CH-CH2-COOH chain] | 5.0 ± 0 | 614 ± 68 | 12050 ± 1835 | 3-6 | 46 ± 26 |

(3.56 mg/kg) (n = 3)
DMSO/PEG400/PBS 1X
(5%/30%/65%) i.v.

TABLE 1-continued

| Compound | | Tmax (min) | Cmax (ng/ml)/ Dose (mg/kg) | Lin-AUC (0-∞) (ng•min/ml)/ Dose (mg/kg) | T-Last (h) | Terminal Half-life elimination, t½z (min) |
|---|---|---|---|---|---|---|
| [structure: 2-Cl-phenyl / 2-MeO-phenyl dioxane with pentenoic acid] | | 5.0 ± 0 | 554 ± 154 | 17416 ± 1734 | 8-12 | 182 ± 55 |
| (3.53 mg/kg) (n = 2) DMSO/PEG400 (5%/95%) i.v. | | | | | | |
| Prodrug from above and the corresponding acid measured i.v. | | 5.0 ± 0 | 272 ± 104 | 15890 ± 1431 | 8 | 345 ± 8 |
| K salt of | | 90 ± 79 | 236 ± 63 | 27195 ± 4453 | 6-12 | 95 ± 34 |
| [structure: 2-Cl-phenyl / 2-HO-phenyl dioxane with pentenoic acid] | | | | | | |
| (10 mg/kg) (n = 3) solid in capsules (p.o.) | | | | | | |
| [structure: 2-Cl-phenyl / 2-MeO-phenyl dioxane with pentenoic acid] | A | 203 ± 137 | 498/dose | 115 816/dose | 12 | 90 ± 17 |
| [structure: 2-Cl-phenyl / 2-MeO-phenyl dioxane with pentenoic acid] | B | 203 ± 137 | 501/dose | 93 700/dose | 12 | 73 ± 22 |
| (10 mg/kg) (n = 4) DMSO/PEG400/PBS (5%/30%/65%) (p.o.) | | | | | | |
| [structure: 2-Cl-phenyl / 2-acetoxy-phenyl dioxane with pentenoic acid] | | 19 ± 8 | 221 ± 182 | 36426 ± 23517 | 24 | 158 ± 51 |
| (10 mg/kg) (n = 4) DMSO/PEG400/PBS (5%/30%/65%) (p.o.) (9.45 mg/kg): | | | | | | |

TABLE 1-continued

| Compound | Tmax (min) | Cmax (ng/ml)/ Dose (mg/kg) | Lin-AUC (0-∞) (ng·min/ml)/ Dose (mg/kg) | T-Last (h) | Terminal Half-life elimination, $t^{1/2}z$ (min) |
|---|---|---|---|---|---|
| and the corresponding acid measured erbumine salt of 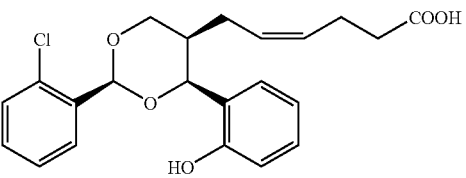 [SMILES: O=C(O)CC/C=C\C[C@@H]1CO[C@H](c2ccccc2Cl)O[C@@H]1c1ccccc1O] (10 mg/kg) (n = 4) solid in capsules (p.o.) | 180 ± 127 | 115 ± 123 | 17352 ± 14479 | 8-12 | 133 ± 45 |
| 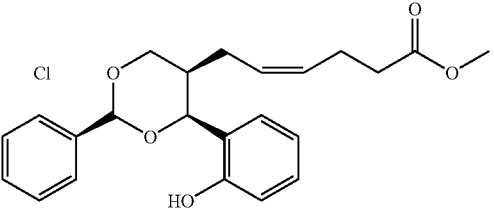 (10 mg/kg) (n = 4) DMSO/PEG400/PBS (5%/30%/65%) (p.o.) (9.70 mg/kg): corresponding acid measured | 73 ± 112 | 104 ± 54 | 17391 ± 5974 | 12 | 100 ± 11 |

The prodrugs of the invention have the advantage of having higher $T_{max}$ or longer half-life before elimination as compared to the corresponding acid. An improved Lin-AUC $(_{0-\infty})$ (ng·min/ml)/Dose (mg/kg) is seen with the prodrugs indicating that exposure to the active component is increased in vivo.

Example 6

Effect on Arterial Thrombosis in a Mouse Model

This example demonstrates an effect of Prodrug 3 on arterial thrombosis in a mouse model. Prodrug 3 is prepared according to Example 3.

Materials
Vehicle (DMSO/PEG 400, 5/95)
Dose of 1, 3, 10, 30, 100 and 300 mg/kg of Prodrug 3 in vehicle
Saline
Aspirin (dose of 100 mg and 600 mg/kg in vehicle)
Aspirin (Aspégic from Sanofi Synthelabo; dissolved in Saline)
Clopidogrel (Plavix from Sanofi Pharma; dissolved in H₂O)

The solutions are diluted 3.3-fold in saline and 100 μl/25 g is injected. Thus, the above-mentioned doses of 100 and 300 mg/kg of compound correspond to final doses of 30 and 100 mg/kg.

It should be noted that PEG is very hygroscopic and that DMSO affects platelet aggregation ex vivo at very low concentration. For i.v. injection in mice this does not appear to be a preferred solvent.

During the experiments, a soluble potassium salt of the drug is provided, diluted in saline. Of this formulation, 100 μl/25 g is injected i.v. in the tail vein (dose of 100 mg/kg).

Thrombosis Model

Solutions are injected (100 μl/25 g body weight) i.v. in the tail vein over 2 min to obtain doses of each compound of 30 mg/kg and 100 mg/kg. Aspirin is given the same way at a dose of 200 mg/kg. Clopidogrel is administered by oral gavage at a dose of 20 mg/kg at 6-7 hours prior to the experiment. The animals assigned to each group are matched for body weight. Mice are typically 8-10 weeks old males and are in a 100% Swiss genetic background.

The arterial thrombosis model is performed essentially as described by Nagai et al. (Nagai N, Lijnen H R, Van Hoef B, Hoylaerts M F, Van Vlijmen B J M. Nutritionally induced obesity reduces the arterial thrombotic tendency of Factor V Leiden mice. Thromb. Haemost, (published on-line; doi: 10.1160/TH07-04-0306). Briefly, a small piece of tissue paper saturated with a 5% FeCl₃ solution is deposited on the isolated femoral artery of the mice for 2 min, followed by extensive washing with saline (application starts at about 10 min after i.v. injection). Blood flow in the hind paws is monitored using a scanning laser Doppler flow meter and digitized images are collected during 30 min at 15 s intervals (starting 1 min after arresting FeCl₃ treatment). The flow in each image is expressed as a percentage of that at the contralateral side, and data are averaged for all 120 images to determine total flow. The same analysis is performed for 10 min intervals (which gives essentially the same information as the area under the curve). The occlusion time is recorded as the first image that showed 0% flow. Flow before treatment is recorded as 100%, and that in occluded arteries as 0%. At the end of the experiment, blood is collected on 0.01M citrate buffer by heart puncture for determination of blood cell counts. Plasma is prepared by centrifugation and stored at −20° C. for determination of drug levels.

Statistical analysis for differences between two groups is performed by non-parametric Student t-test. Occlusion times >30 min were considered equal to 30 min for statistical analysis. Significance is set at p<0.05.

Results

A total of about 60 mice are used in this study, of which 4 in the preliminary experiments to optimize the administration scheme.

Occlusion Times

Aspirin at 200 mg/kg has no effect on the occlusion time; the somewhat shorter occlusion time as compared to vehicle is due to two experiments with delayed occlusion in the vehicle group (mean±SEM=7'18"±0'33" without these)

Clopidogrel totally prevents occlusion within 30 min in 6/7 experiments. In one experiment rapid occlusion is observed Prodrug 3 at a dose of 30 mg/kg in vehicle prolongs the occlusion time as compared to aspirin (p=0.024) and the parent compound, but has no effect as compared to vehicle.

Blood Flow

Aspirin at 200 mg/kg has no significant effect on the total blood flow (p=0.53 versus vehicle).

Clopidogrel significantly improved total blood flow (p=0.0087, versus vehicle, including experiment B130).

Prodrug 3 at a dose of 10 mg/kg in vehicle has no effect on total blood flow (p=0.84 versus vehicle and p=0.65 versus aspirin).

Prodrug 3 at a dose of 30 mg/kg in vehicle slightly improved total blood flow as compared to aspirin (p=0.055), but not as compared to vehicle (p=0.45).

Example 7

PPAR Gamma Binding Assay

This example demonstrates that Prodrug 2 binds to human recombinant PPAR gamma. Prodrug 2 is prepared according to Example 3.

Human Recombinant (*E. coli*) PPARgamma) (h) Binding Assay:

Ligand Concentration: [3H]-rosiglitazone 10 nM

Non Specific Binding: rosiglitazone (10 µM)

Incubation: 120 min. at 4° C.

The results are expressed as a percent of control specific binding ((measured specific binding/control specific binding)×100) obtained in the presence of the test compounds. The $IC_{50}$ values (concentration causing a half-maximal inhibition of control specific binding) and Hill coefficients (nil) were determined by non-linear regression analysis of the competition curves generated with mean replicate values using Hill equation curve fitting $(Y=D+[(A-D)/(1+(C/C_{50})nH)]$, where Y=specific binding, D=minimum specific binding, A=maximum specific binding, C=compound concentration, $C_{50}=IC_{50}$, and nH=slope factor). This analysis is performed using a software developed at Cerep (Hill software) and validated by comparison with data generated by the commercial software SigmaPlot® 4.0 for Windows® (© 1997 by SPSS Inc.). The inhibition constants (Ki) are calculated using the Cheng Prusoff equation $(Ki=IC_{50}/(1+(L/KD))$, where L=concentration of radioligand in the assay, and KD=affinity of the radioligand for the receptor). The data shows that Prodrug 2 binds to PPARgamma at least as well as the corresponding acid prepared in Example 1, and that the prodrug is converted to the corresponding acid.

Example 8

Thromboxane receptor binding assays were performed as described in Example 6

TP Receptor Radioligand Binding Studies:

Using these experimental conditions Human recombinant HEK-293 cells, Ligand: 5 nM [$^3$H] SQ-29548, Vehicle: 1% DMSO, Incubation Time, Temp: 30 min at 25° C., Incubation Buffer: 50 mM Tris-HCl, pH 7.4, 154 mM NaCl, Non-Specific Ligand: 1 µM SQ-29548, KD: 9.4 nM, Bmax: 5.1 pmole/mg protein, Specific Binding: 93%, the assay performed according to Hedberg A, Hall S E, Ogletree M L, Harris D N and Liu E C-K (1988) Characterization of [5, 6-3H]SQ 29,548 as a high affinity radioligand, binding to thromboxane A2/prostaglandin H2-receptors in human platelets. J Pharmacol Exp Ther. 245(3):786-92792, and Saussy D L Jr, Mais D E, Burch R M and Halushka P V (1986) Identification of a putative thromboxane A2/prostaglandin H2 receptor in human platelet membranes. J Biol Chem. 261(7):3025-9.

Human Platelet Thromboxane Synthase Assay:

Using these experimental conditions Substrate: 10 µM $PGH_2$, Vehicle: 1% DMSO

Pre-incubation time, temp: 15 min at 25° C., Incubation time, temp: 3 min at 25° C.

Incubation Buffer: 10 mM Tris-HCl, pH 7.4, Quantification Method: EIA quantification of $TxB_2$, the assay performed according to Borsch-Haubold A G, Pasquet S, Watson S P. (1998) Direct inhibition of cyclooxygenase-1 and -2 by the kinase inhibitors SB 203580 and PD 98059. SB 203580 also inhibits thromboxane synthase. J Biol Chem. 273(44): 28766-72, and Iizuka K, Akahane K, Momose D, Nakazawa M, Tanouchi T, Kawamura M, Ohyama I, Kajiwara I, Iguchi Y, Okada T, Taniguchi K, Miyamoto T, Hayashi M. (1981) Highly selective inhibitors of thromboxane synthetase. 1. Imidazole derivatives. J Med Chem. 24(10):1139-48.

TP Receptor Platelet Aggregation—Rabbit:

Using these experimental conditions New Zealand Rabbit (2.75±0.25 kg) platelet rich plasma, Vehicle: 0.3% DMSO, Assay: Inhibition of 1.5 µM U-46619-induced platelet aggregation, Incubation Time, Temp: 5 min at 37° C., Incubation Buffer: Trisodium Citrate (0.13 M)-treated platelet rich plasma, Bath Volume: 0.5 mL, Time of Assessment: 5 min, Quantification Method: Optical Density Change. the assay performed according to Patscheke, H., and Stregmeier, K. (1984) Investigations on a selective non-prostanoic thromboxane antagonist, BM13,177, in human platelets. Thrombosis Research 33:277-288

TP Receptor Platelet Aggregation—Human:

Using these experimental conditions Human (60±10 kg) platelet rich plasma, Vehicle: 0.3% DMSO, Assay: Inhibition of 3 µM U-46619-induced platelet aggregation, Incubation Time, Temp: 5 min at 37° C., Incubation Buffer: Trisodium Citrate (0.13M)-treated fresh platelet rich plasma, Bath Volume: 0.5 mL, Time of Assessment: 5 minutes, Quantification Method: Optical Density Change the assay performed according to Patscheke, H., and Stregmeier, K. (1984) Investigations on a selective non-prostanoic thromboxane antagonist, BM13,177, in human platelets. Thrombosis Research 33:277-288

$IC_{50}$ Calculation:

The data were transformed to semi-log and then analysed using non-linear regression to a four-parameter dose-response curve $Y=Bottom+(Top-Bottom)/(1+10\hat{\ }((Log\ EC_{50}-X)*HillSlope))$ using the log(agonist) vs. response—Variable slope function of GraphPad Prism software (http://graphpad.com/help/prism5/prism5help.html? usingnonlinear_regression_step_by_s.ht m).

| Compound: | Platelet aggregation | | | Thromboxane receptor (TP) binding | | | Thromboxane synthase Human platelet | |
|---|---|---|---|---|---|---|---|---|
| | Human | Rabbit | | Human recombinant HEK-293 cells | | | | |
| | Inhibition (%) at | IC$_{50}$ (nM) | Inhibition (%) at | | Inhibition (%) | | Inhibition | IC$_{50}$ |
| | | | 10 μM | 30 μM | @ 10 μM | IC$_{50}$ (nM) | Ki (nM) | (%) at 5 μM | (nM) |
| A | 13 @ 30 μM | | | 15 @ 0.1 mM | 94, 96 | 1260 | 825 | 25, 28 @ 10 μM | 12100 |
| B | 94 @ 1 μM<br>97 @ 8 μM<br>100 @ 16 μM | 310 | | 100 | 102 | 0.84 | 0.55 | 43, 61 @ 10 μM | 7020 |
| 3 | | | 33 | | 98 | | | 12 | |
| 4 | | | | | 85 | 1870 | 1220 | 52 @ 30 μM | 17500 |
| 5 | | | | | 96 @ 0.3 μM | 23.4 | 15.3 | 62 @ 30 μM | 20400 |
| Picotamide | | | | 36, 21 @ 0.1 mM | 66 | 5950 | 3880 | 53 at 10 μM | 10100 |

Compound A: (Z)-6-((2R,4R,5S)-2-(2-chlorophenyl)-4-(2-hydroxyphenyl)-1,3-dioxan-5-yl)hex-4-enoic acid (enantiomer 2)
Compound B: (Z)-6-((2S,4S,5R)-2-(2-chlorophenyl)-4-(2-hydroxyphenyl)-1,3-dioxan-5-yl)hex-4-enoic acid (enantiomer 1)
Compound 3: (Z)-6-(-2-(2-chlorophenyl)-4-(2-methoxyphenyl)-1,3-dioxan-5-yl)hex-4-enoic acid
Compound 4: (Z)-6-((2R,4R,5S)-2-(2-chlorophenyl)-4-(2-methoxyphenyl)-1,3-dioxan-5-yl)hex-4-enoic acid
Compound 5: (Z)-6-((2S,4S,5R)-2-(2-chlorophenyl)-4-(2-methoxyphenyl)-1,3-dioxan-5-yl)hex-4-enoic acid.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

The invention claimed is:
1. A compound of formula (III)

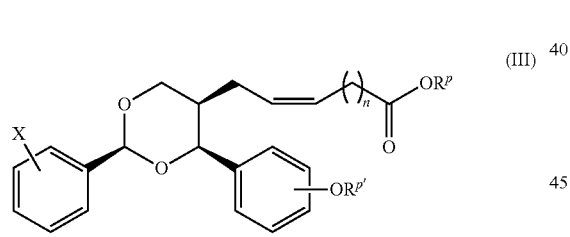

or a pharmaceutically acceptable salt thereof wherein
X is hydrogen, halogen, cyano, nitro, hydroxyl, haloalkyl, alkyl, or O—R where R is a lower alkyl group;
n is 0, 1, 2, 3, 4, or 5; and
$R^p$ is H, lower alkyl, or a progroup selected from ($C_2$-$C_{12}$)alkanoyloxymethyl, 1-alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy) ethyl having from 4 to 7 carbon atoms, 1-methyl-1-(alkoxycarbonyloxy) ethyl having from 5 to 8 carbon atoms, N-(alkoxycarbonyl) aminomethyl having from 3 to 9 carbon atoms, 1-(N (alkoxycarbonyl)amino)ethyl having from 4 to 10 carbon atoms, 3-phthalidyl, 4 crotonolactonyl, gamma-butyrolacton-4yl, di-N,N-($C_1$-$C_2$)alkylamino($C_2C_3$)alkyl, carbamoyl-($C_1$-$C_2$)alkyl, N,N-di($C_1$-$C_2$)alkylcarbamoyl-($C_1$-$C_2$)alkyl and piperidino-, pyrrolidino- or morpholino ($C_2$-$C_3$)alkyl;

$R^{p'}$ is H, lower alkyl, or a progroup selected from

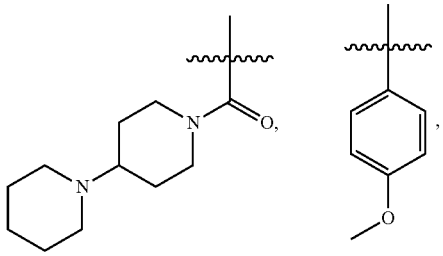

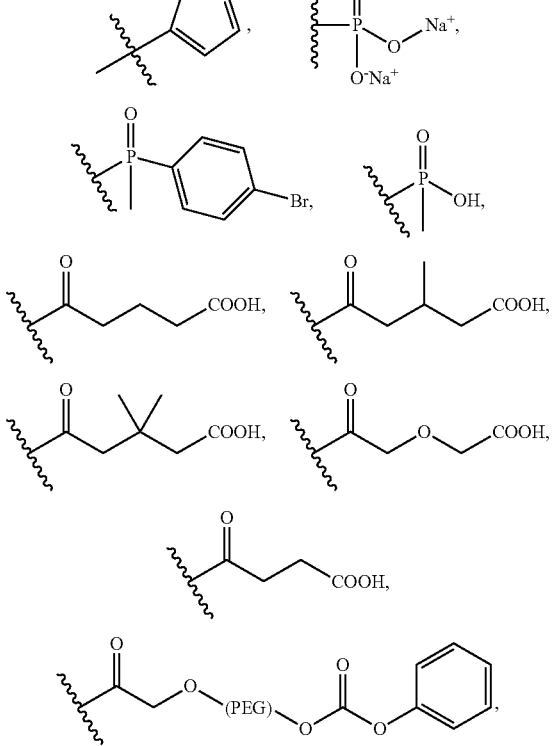

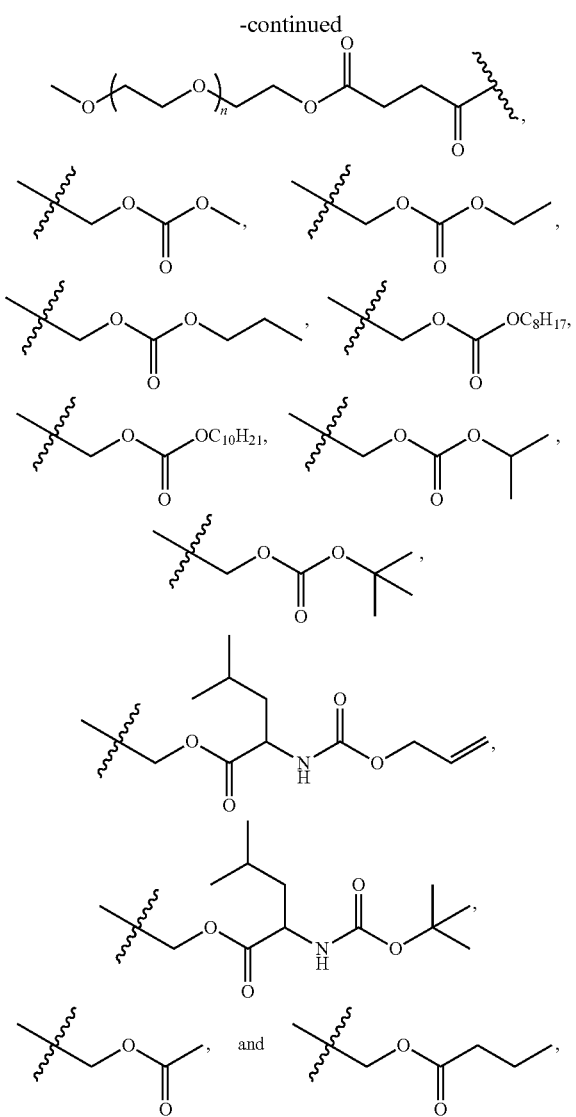

provided that
R$^P$ is not H or lower alkyl when R$^{P'}$ is H; and R$^{P'}$ is not H or lower alkyl when R$^P$ is H.

2. The compound or pharmaceutically acceptable salt according to claim 1, wherein n is 1 or 2.

3. The compound or pharmaceutically acceptable salt according to claim 2, wherein n is 2, and X is chloro.

4. The compound or pharmaceutically acceptable salt according to claim 3, wherein R$^P$ is H and R$^{P'}$ is a prodrug group.

5. The compound of claim 3 wherein R$^{P'\ is\ H\ and\ Rp}$ is a progroup.

6. The compound of claim 3 wherein both R$^P$ and R$^{P'}$ are progroups and only one of the progroups is lower alkyl, aryl.

7. The compound of claim 6, wherein R$^{P'}$ is lower alkyl.

8. The compound of claim 6, wherein R$^P$ is lower alkyl.

9. A method of treating a diabetic patient who is risk of developing myocardial infarction, thrombosis, thrombotic disorders, stent triggered thrombus formation, stent induced restenosis, stent-triggered hyperplasia, pulmonary hypertension, atherosclerosis, diabetic nephropathy, retinopathy, diabetic retinopathy, peripheral arterial disease, lower limb circulation, pulmonary embolism, thrombus formation, hyperplasia, septic shock, preeclampsia, asthma, rhinitis, allergic rhinitis, tumour angiogenesis and metastasis comprising administering to the patient a compound or salt according to claim 1.

10. The method of claim 9, wherein n is 2, and X is chloro.

11. The method of claim 10, wherein Rp is H and R$^{P'}$is a prodrug group.

12. The method of claim 10, wherein Rp' is H and R$^P$ is a prodrug group.

13. A compound or pharmaceutically acceptable salt according to claim 1, wherein R$^P$ is methyl, n is 2, and X is chloro where X is in the ortho position relative to the point of attachment of the phenyl carrying X to the dioxane ring.

14. A compound or pharmaceutically acceptable salt according to claim 1, wherein R$^P$ is H, n is 2, and X is chloro where X is in the ortho position relative to the point of attachment of the phenyl carrying X to the dioxane ring.

15. A compound or pharmaceutically acceptable salt thereof according to claim 1, wherein the compound is:

-continued
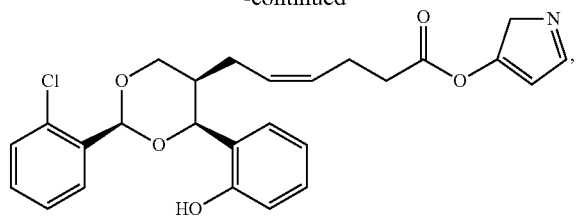
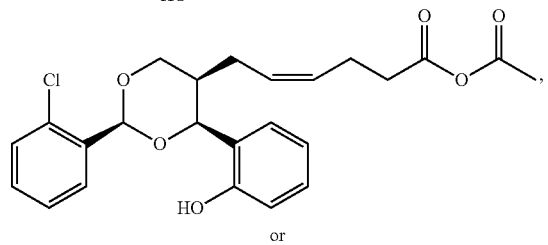
or
-continued
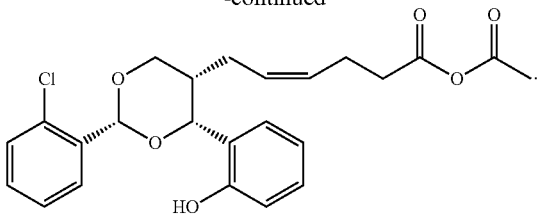
16. A pharmaceutical composition comprising a compound according to claim 1.
17. A method of treating an infection in a patient comprising administering to the patient a compound or salt according to claim 1.
18. A method of treating cancer in a patient comprising administering to the patient a compound or salt according to claim 1.
* * * * *